United States Patent
Cai

(10) Patent No.: US 10,047,386 B2
(45) Date of Patent: Aug. 14, 2018

(54) BIOMARKER FOR ABDOMINAL AORTIC ANEURYSM

(71) Applicant: THE REGENTS OF THE UNIVERSITY OF CALIFORNIA, Oakland, CA (US)

(72) Inventor: Hua Cai, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 105 days.

(21) Appl. No.: 14/349,828

(22) PCT Filed: Oct. 11, 2012

(86) PCT No.: PCT/US2012/059805
§ 371 (c)(1),
(2) Date: Apr. 4, 2014

(87) PCT Pub. No.: WO2013/055954
PCT Pub. Date: Apr. 18, 2013

(65) Prior Publication Data
US 2014/0308686 A1    Oct. 16, 2014

Related U.S. Application Data

(60) Provisional application No. 61/545,975, filed on Oct. 11, 2011.

(51) Int. Cl.
*G01N 33/573*    (2006.01)
*G01N 33/68*    (2006.01)
(Continued)

(52) U.S. Cl.
CPC ............... *C12Q 1/008* (2013.01); *C12Q 1/37* (2013.01); *G01N 33/5735* (2013.01);
(Continued)

(58) Field of Classification Search
CPC ....... C12Q 1/008; G01N 33/573; G01N 33/68
See application file for complete search history.

(56) References Cited

U.S. PATENT DOCUMENTS

| 2002/0052374 A1 | 5/2002 | Rabelink et al. |
| 2007/0032533 A1 | 2/2007 | Garvey et al. |
| (Continued) | | |

FOREIGN PATENT DOCUMENTS

| WO | 2009048884 A1 | 4/2009 |
| WO | 2010080452 A2 | 7/2010 |

OTHER PUBLICATIONS

Kuhlencordt et al., "Accelerated Atherosclerosis, Aortic Anurysm Formation, and Ischemic Heart Disease in Apolipoprotein E/Endothelial Nitric Oxide Synthase Double-Knockout Mice," Circulation, pp. 448-454, published 2001.*

(Continued)

*Primary Examiner* — Tracy Vivlemore
*Assistant Examiner* — Nam P Nguyen
(74) *Attorney, Agent, or Firm* — Karen S Canady; canady + lortz LLP

(57) ABSTRACT

Methods for detecting abdominal aortic aneurysm (AAA) or predisposition to AAA in a apoE subject, methods for monitoring the efficacy of treatment of AAA in a subject, and methods for evaluating the severity of AAA or risk of AAA in a subject involve measuring the amount of tetrahydrobiopterin (H4B) present in the test sample and comparing it to the amount of H4B present in a standard or previous test sample. A decreased amount of H4B present in the test sample compared to the standard is indicative of AAA or predisposition to AAA. Treatment can be administered to the subject prior to a second time point, and an increased amount of H4B present in the second test sample compared to the first test sample is indicative of effective treatment of (Continued)

AAA. Candidates can be identified for further testing or monitoring for AAA, and/or for treatment for AAA.

18 Claims, 11 Drawing Sheets

(51) Int. Cl.
    *C12Q 1/00*     (2006.01)
    *C12Q 1/37*     (2006.01)

(52) U.S. Cl.
    CPC ... *G01N 33/6893* (2013.01); *G01N 2800/329* (2013.01); *G01N 2800/50* (2013.01); *G01N 2800/56* (2013.01); *Y10T 436/147777* (2015.01)

(56) References Cited

U.S. PATENT DOCUMENTS

2008/0175924 A1*   7/2008   Clelland ............ A61K 31/7052
                                                    424/677
2010/0260747 A1   10/2010   Schiffmann et al.

OTHER PUBLICATIONS

Stroes et al., "Folic Acid Reverts Dysfunction of Endothelial Nitric Oxide Synthase," Circulation Research, pp. 1129-1134, published Jun. 9, 2000.*
Pimiento et al., "Endothelial Nitric Oxide Synthase Stimulates Aneurysm Growth in Aged Mice", J Vasc Res., vol. 45, pp. 251-258, published Jan. 10, 2008.*
Fekkes et al., "Quantitation of total biopterin and tetrahydrobiopterin in plasma", Clinical Biochemistry, vol. 40, pp. 411-413, published online Jan. 5, 2007.*
Galloway et al., "Serum Biopterin as a Marker of Immune Activation in the Spontaneously Diabetic BB rat", Pteridines, vol. 9, no1. 4, pp. 222-228, published 1998.*
WebMD (Aortic Aneurysm: Abdominal and Thoracic), published Oct. 1, 2010, retrieved from http://web.archive.org/web/20101001083211/http://www.webmd.com/heart-disease/tc/aortic-aneurysm-overview (2 pages).*
Moat et al., "Folic acid reverse endothelial dysfunction induced by inhibition of tetrahydrobiopterin biosynthesis", European Journal of Pharmacology, vol. 530, pp. 250-258, published 2006.*
Shinozaki et al., "Coronary Endothelial Dysfunction in the Insulin-Resistant State Is Linked to Abnormal Pteridine Metabolism and Vascular Oxidative Stress" JACC, vol. 38, No. 7, pp. 1821-1828, published Dec. 2001.*
Chalupsky, Karel., et al., "Intrinsic eNOS dysfunction causes vascular remodeling and abdominal aortic aneurysm", Mar. 2006, FASEB Journal—Meeting Abstract, 20: A1161.
Crabtree, Mark J., et al., "Dihydrofolate reductase protects endothelial nitric oxide synthase from uncoupling in tetrahydrobiopterin deficiency", Mar. 2011, Free Radical Biology & Medicine, 50(2011): 1639-1646.
Galley, H.F., et al., "Circulating tetrahydrobiopterin concentrations in patients with septic shock", 2001, British Journal of Anaesthesia, 86(4): 578-80.
Gao, Ling, et al., "Role of uncoupled endothelial nitric oxide synthase in abdominal aortic aneurysm formation: treatment with folic acid", Nov. 14, 2011, Hypertension, 59(1): 158-66.
Kaneko, Y.S. et al., "Determination of tetrahydrobiopterin in murine locus coeruleus by HPLC with fluorescence detection", Aug. 2001, Brain Research Protocols, 8(1): 25-31.v. 14, 2011, Hypertension, 59(1): 158-66.
Liao, Ming-fang, et al., "Role of nitric oxide and inducible nitric oxide synthase in human abdominal aortic aneurysms: a preliminary study", 2006, Chinese Medical Journal, 119(4): 312-318.
Schmidt, Tim S., et al., "Mechanisms for the role of tetrahydrobiopterin in endothelial function and vascular disease", 2007, Clinical Science, 113: 47-63.
Ueda, Seiji, et al., "Tetrahydrobiopterin Restores Endothelial Function in Long-Term Smokers", 1999, Journal of the American College of Cardiology, 35(1): 71-5.
Xiong, Wanfen, et al., "Inhibition of reactive oxygen species attenuates aneurysm formation in a murine model", Jan. 2009, Atherosclerosis, 202(1): 128-134.
International Search Report + Written Opinion dated Jan. 31, 2013 in PCT Application No. PCT/US2012/059805, filed Oct. 11, 2012.

* cited by examiner

BIOMARKER FOR ABDOMINAL AORTIC ANEURYSM

This application claims the benefit of U.S. provisional patent application Ser. No. 61/545,975, filed Oct. 11, 2011, the entire contents of which are incorporated herein by reference. Throughout this application various publications are referenced. The disclosures of these publications in their entireties are hereby incorporated by reference into this application in order to describe more fully the state of the art to which this invention pertains.

STATEMENT REGARDING FEDERALLY SPONSORED RESEARCH

This invention was made with Government support under HL077440, awarded by the National Institutes of Health. The Government has certain rights in the invention.

TECHNICAL FIELD OF THE INVENTION

The present invention relates generally to a novel biomarker for abdominal aortic aneurysm and methods of using this biomarker to detect and monitor a patient's risk for aneurysm.

BACKGROUND OF THE INVENTION

Abdominal aortic aneurysm (AAA) is a severe human vascular disease with unclear molecular mechanisms. It is defined by histopathologic remodeling within the aortic wall, associated with progressive aortic dilatation and eventual rupture. Male gender and cigarette smoking are the only known risk factors for AAA. Approximately one in every 250 people over the age of 50 will die of a ruptured AAA. However for this prevalent and life threatening disease the only cure so far is surgical correction, due to lack of insights into its disease mechanisms. Furthermore, surgery is only recommended for AAA that is bigger than 5.5 cm; and that smaller AAA with no symptoms often cannot be diagnosed, resulting in silent growth and surprising lethal rupture. Therefore it is of public health significance to advance our understanding of AAA etiology, which may result in innovative therapeutic and preventive strategies.

There remains a need for biomarkers for AAA. In particular, there remains a need for biomarkers that can be used for screening, detecting and monitoring of AAA, as well as identifying those predisposed to developing AAA.

SUMMARY OF THE INVENTION

The invention provides a method for detecting abdominal aortic aneurysm (AAA) or predisposition to AAA in a subject. The method comprises (a) contacting a test sample from the subject with an assay device capable of measuring the amount of tetrahydrobiopterin ($H_4B$) present in the test sample; and (b) comparing a measured amount of $H_4B$ present in the test sample to a standard amount of $H_4B$. In a typical embodiment of the invention, the sample comprises serum or whole blood. A decreased amount of $H_4B$ present in the test sample compared to the standard is indicative of AAA or predisposition to AAA. In some embodiments, a statistically significant decrease in the amount of $H_4B$ present in the test sample compared to the standard is indicative of AAA or predisposition to AAA. In other embodiments, the decrease in $H_4B$ is at least about a 10% decrease compared to the standard, or at least a 20%, 30%, 40%, 50% or 60%, 70%, 80% or 90% decrease. Smaller decreases are generally indicative of a predisposition to AAA, while larger decreases are more likely to indicate the presence of AAA.

Accordingly, the method can further comprise identifying a subject as a candidate for further testing or monitoring for AAA, such as by ultrasound or by repeated testing for $H_4B$ after one or more designated intervals. The method can also further comprise prescribing treatment for AAA to the subject whose $H_4B$ is decreased compared to the standard. Examples of the treatment comprise folic acid therapy, and/or DHFR therapy, including gene therapy.

Also provided is a method for monitoring the efficacy of treatment of AAA in a subject. In one embodiment, the method comprises (a) contacting a first test sample from the subject obtained at a first time point with an assay device capable of measuring the amount of $H_4B$ present in the test sample; (b) contacting a second test sample from the subject obtained at a second time point with an assay device capable of measuring the amount of $H_4B$ present in the test sample; and (c) comparing the measured amount of $H_4B$ present in the first and second test samples. Treatment is administered to the subject prior to the second time point, and an increased amount of $H_4B$ present in the second test sample compared to the first test sample is indicative of effective treatment of AAA. This method can be initiated at the onset of treatment, or after a treatment plan is already underway. In some embodiments, a statistically significant increase in the amount of $H_4B$ present in the second sample compared to the first sample is indicative of effective treatment of AAA. In other embodiments, the increase in $H_4B$ is at least about a 10% increase compared to the first sample, or at least a 20%, 30%, 40%, 50% or 60%, 70%, 80%, 90%, 100%, 150%, 200% or greater increase. The method optionally further comprises prescribing a modified treatment for AAA to the subject whose $H_4B$ is decreased or increased compared to the first sample or compared to a standard.

The invention additionally provides a method for evaluating the severity of abdominal aortic aneurysm (AAA) or risk of AAA in a subject. In one embodiment, the method comprises (a) contacting a test sample from the subject with an assay device capable of measuring the amount of $H_4B$ present in the test sample; (b) measuring the amount of $H_4B$ present in the test sample; and (c) comparing the measured amount of $H_4B$ present in the test sample to a measured amount of $H_4B$ present in a standard. The extent of decrease in the amount of $H_4B$ present in the test sample compared to the standard is indicative of the severity or risk of AAA in the subject. In some embodiments, a statistically significant decrease in the amount of $H_4B$ present in the test sample compared to the standard is indicative of AAA or predisposition to AAA. In other embodiments, the decrease in $H_4B$ is at least about a 10% decrease compared to the standard, or at least a 20%, 30%, 40%, 50% or 60%, 70%, 80% or 90% decrease. Smaller decreases are generally indicative of a predisposition to, or a milder case of AAA, while larger decreases are more likely to indicate the presence of AAA, or a more severe case of AAA. Depending on the amount of $H_4B$ present in the test sample, the subject may be monitored or treated as described herein.

In a typical embodiment, the assay device comprises a high performance liquid chromatography (HPLC) column, or an immunoassay kit, such as an enzyme-linked immunosorbent assay (ELISA) kit, a chemiluminescence assay kit, or other conventional assay kit. Accordingly, the invention further provides a kit comprising reagents and/or an assay device for use in detection of $H_4B$.

BRIEF DESCRIPTION OF THE FIGURES

FIG. 1A is a digital photograph with insets of digital photomicrographs showing representative appearance of abdominal aortas in the different experimental groups of WT, WT/Ang II, hph-1, and hph-1/Ang II by day 14. Only Ang II-infused hph-1 mice developed AAA, with visible evidence of hemorrhage. Hematoxylin-eosin staining (arrows) of the AAA segment revealed thrombus formation. FIG. 1B is a pie chart showing AAA morbidity and mortality rates (no-AAA vs nonlethal AAA vs lethal AAA) in Ang II-infused hph-1 mice at 21%, 65%, and 14%, respectively. FIG. 1C is a graph depicting changes in mean blood pressure (MBP) in Ang II-infused hph-1 mice. The MBP was monitored by an intracarotid telemetry method (Data Sciences International) continuously for 14 days.

FIG. 2A shows aortic $H_4B$ content; FIG. 2B shows aortic $NO^{\bullet}$ production; and FIG. 2C shows aortic superoxide ($O_2^{\bullet-}$) production in the presence or absence of L-NG-nitro-L-arginine methyl ester (L-NAME). $P<0.05$.

FIG. 3A shows endothelial and nonendothelial DHFR expression in aortic preparations; FIG. 3B shows aortic tetrahydrobiopterin ($H_4B$) content; and FIG. 3C shows aortic eNOS uncoupling activity (indicated by NG-nitro-L-arginine methyl ester [L-NAME]-sensitive $O_2^{\bullet-}$ production). *$P<0.01$.

(FIG. 6B) Verhoeff-Van Gieson (VVG) staining (black arrows showing elastin changes); and (FIG. 6C) macrophage staining indicating macrophage infiltration.

FIG. 7A, Representative zymogram showing MMP2 and MMP9 activities. FIG. 7B, Quantitative data of MMP2 activity. FIG. 7C, Quantitative data of MMP9 activity. *$P<0.05$ vs sham.

FIG. 9A shows measurements made from angiotensin II (Ang II)-infused hph-1 mice (n=3-4), while FIG. 9B shows measurements made from Ang II-infused apoE null mice (n=5-6). The AAA is usually examined by week 4 with an incidence rate of ~92% in Ang II-infused apoE mice, and the vessels already undergo severe remodeling and AAA development at week 3. The correlated decline in circulating and aortic $H_4B$ further demonstrate that circulating $H_4B$ can serve as a predictive and diagnostic marker for AAA.

FIG. 10A shows measurements made from hph-1 animals (n=3-4), while FIG. 10B shows measurements made from apoE animals (n=5-6). In both AAA models, circulating/plasma $H_4B$ is nicely correlated with aortic levels of $H_4B$, validating a biomarker role of circulating/plasma $H_4B$ for AAA formation, which has been linked to aortic deficiency in $H_4B$.

FIG. 13A shows representative ESR spectra of NO. FIG. 13B shows grouped data of aortic NO levels (n=6).

DETAILED DESCRIPTION

Figures 1A, 1B, 1C:
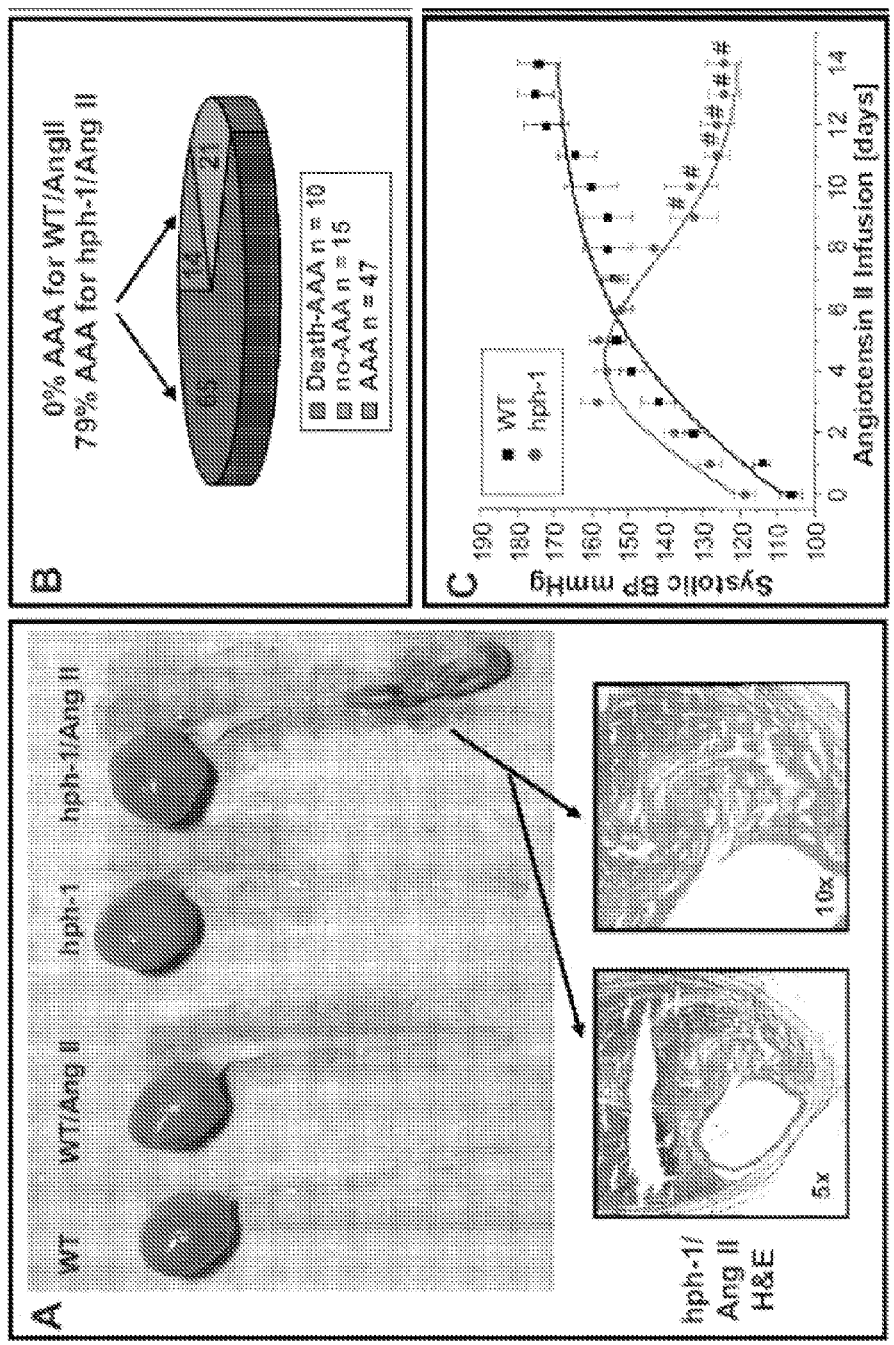
FIGS. 1A-C show that angiotensin II (Ang II) induces abdominal aortic aneurysm (AAA) formation in hyperphenylalaninemia (hph)-1 mice. Wild-type (WT) and hph-1 mice were infused with Ang II (0.7 mg/kg per day) for 14 days.

The present invention is based on the discovery that plasma levels of tetrahydrobiopterin ($H_4B$) correlate with tissue levels of $H_4B$, and hence can be utilized as a novel biomarker for AAA development, and as an indicator of treatment efficacy. Using two different models of AAA, namely angiotensin II infused hph-1 and apoE null mice, the examples described below demonstrate that plasma levels of $H_4B$ correlate well with tissue $H_4B$ levels, both of which were decreased in AAA and were restored by folic acid treatment. The invention thus provides a method of screening for $H_4B$ in the blood, plasma, or other body fluid samples of subjects, offering an innovative, convenient and powerful predictor of AAA development. This screening is of particular value for use with populations at risk for AAA, such as older males who smoke. Moreover, the screening method of the invention is much more predictive of AAA than currently identified risk factors, such as smoking, age and gender.

Oral administration of folic acid leads to recoupling of eNOS and consequent reduction in oxidative stress and improvement in nitric oxide bioavailability, which in turn prevents vascular remodeling that precedes AAA. This results from folic acid upregulation of the eNOS cofactor salvage enzyme dihydrofolate reductase (DHFR). Thus, subjects identified via $H_4B$ testing in accordance with the invention can be treated with folic acid or other therapies that promote DHFR, such as DHFR gene therapy. This early detection can reduce or eliminate the need for surgical repair and the risk of rupture.

Definitions

All scientific and technical terms used in this application have meanings commonly used in the art unless otherwise specified. As used in this application, the following words or phrases have the meanings specified.

As used herein, an "assay device" refers to an analytic instrument or apparatus customarily used to analyze, measure and/or detect the presence of a chemical substance. A typical example of such an instrument is a high performance liquid chromatography (HPLC) column. Other chromatography instruments can be used, as well as an immunoassay or other conventional detection assay. A typical example of an immunoassay is an ELISA.

As is understood by those skilled in the art, a sample obtained from a subject may be brought into contact with an analytic instrument either directly, or after first being brought into contact with a solvent or other preparatory medium.

As used herein, a "control" sample is typically one obtained from one or more normal, healthy subjects, or where appropriate, from the same subject but at a time when the subject was known to be in a healthy condition. Also suitable as a control for comparison is an accepted normal level of the referenced analyte, referred to herein as a "standard".

As used herein, "pharmaceutically acceptable carrier" or "excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences*, 18th edition, A. Gennaro, ed., Mack Publishing Co., Easton, Pa., 1990).

As used herein, "a" or "an" means at least one, unless clearly indicated otherwise.

Methods

The invention provides a method for detecting abdominal aortic aneurysm (AAA) or predisposition to AAA in a subject. The method comprises (a) contacting a test sample from the subject with an assay device capable of measuring the amount of tetrahydrobiopterin ($H_4B$) present in the test sample; and (b) comparing a measured amount of $H_4B$ present in the test sample to a standard amount of $H_4B$. A decreased amount of $H_4B$ present in the test sample compared to the standard is indicative of AAA or predisposition to AAA. In some embodiments, a statistically significant decrease in the amount of $H_4B$ present in the test sample compared to the standard is indicative of AAA or predisposition to AAA. Differences in circulating $H_4B$ levels in the range of ~1 to 6 pmol/mg can be detected. In some embodiments, a decrease in $H_4B$ levels to less than about 3 pmol/mg is indicative of AAA, and levels below ~2 pmol/mg are indicative of severe AAA. In other embodiments, the decrease in $H_4B$ is at least about a 10% decrease compared to the standard, or at least a 20%, 30%, 40%, 50% or 60%, 70%, 80% or 90% decrease. Smaller decreases, such as to the range of about 2.9-2.0 pmol/mg, are generally indicative of a predisposition to AAA, while larger decreases, such as to less than about 1.9 pmol/mg, are more likely to indicate the presence of AAA. The amount of circulating $H_4B$ correlates with the size of the aneurysm.

In some embodiments, the standard amount of $H_4B$ used for reference is adopted from a level accepted by those skilled in the art as normal for healthy subjects free of AAA this would vary depending on age and gender. In other embodiments, the standard used for comparison in the method is a sample obtained from normal, healthy control subjects. In yet other embodiments, the standard used for comparison is a test sample taken previously from the same subject at a time when the subject was known to be free of disease. Additional useful sources of reference levels for comparison include aneurismal and adjacent tissues routinely collected during open AAA repair surgery, as well as blood, plasma, or other body fluid samples collected prior to surgery. Thus, in some embodiments, the level of $H_4B$ in the test sample obtained from the subject is compared to both normal standard levels of $H_4B$ and known abnormal levels obtained from AAA samples.

Optionally, the method can further comprise identifying a subject as a candidate for further testing or monitoring for AAA, such as by ultrasound or by repeated testing for $H_4B$ after one or more designated intervals. For example, subjects with more severe cases may be monitored monthly, while those with mild cases may be monitored every three months. The treating physician will be able to adjust this schedule based on the needs and risks for an individual patient. Thus, the method can be repeated and the measured amount of $H_4B$ can be compared either to the standard or to a previous measurement from the same subject. Initial monitoring may comprise repeat testing for $H_4B$, and the subject can be referred for treatment and/or ultrasound evaluation after $H_4B$ testing indicates significant progression toward AAA. Measuring changes in $H_4B$ levels can detect AAA before it can be detected via ultrasound. Early detection of AAA allows for less aggressive treatment and avoidance of surgery. For example, if a subject exhibits an initial 5-10% reduction, is later observed to show a 15% reduction after a follow-up period, the subject needs to be monitored more frequently than those who do not show any reduction or a steady level of small reduction of <10% over time.

The method can further comprise prescribing treatment for AAA to the subject whose $H_4B$ is decreased compared to the standard. Examples of the treatment comprise folic acid therapy, and/or dihydrofolate reductase (DHFR)-targeting therapies, including gene therapies, and any pharmacological or other therapies effective in improving DHFR function, which will result in improved $H_4B$ levels and prevention, delay or amelioration of AAA. Likewise, treatment can comprise other countermeasures directed at eNOS uncoupling.

Also provided is a method for monitoring the efficacy of treatment of AAA in a subject. In one embodiment, the method comprises (a) contacting a first test sample from the subject obtained at a first time point with an assay device capable of measuring the amount of $H_4B$ present in the test sample; (b) contacting a second test sample from the subject obtained at a second time point with an assay device capable of measuring the amount of $H_4B$ present in the test sample; and (c) comparing the measured amount of $H_4B$ present in the first and second test samples. Preferably, identical or nearly identical assay device and conditions are used for obtaining the first and second test samples. Treatment is administered to the subject prior to the second time point, and an increased amount of $H_4B$ present in the second test sample compared to the first test sample is indicative of effective treatment of AAA.

The method of monitoring efficacy of treatment can be initiated at the onset of treatment, or after a treatment plan is already underway. In some embodiments, a statistically significant increase in the amount of $H_4B$ present in the second sample compared to the first sample is indicative of effective treatment of AAA. In other embodiments, the increase in $H_4B$ is at least about a 10% increase compared to the first sample, or at least a 20%, 30%, 40%, 50% or 60%, 70%, 80%, 90%, 100%, 150%, 200% or greater increase. The method optionally further comprises prescribing a modified treatment for AAA to the subject whose $H_4B$ is decreased or increased compared to the first sample or compared to a standard. For example, the treatment can be modified by increasing or decreasing the amount of folic acid or other therapeutic agent administered to the subject.

The invention additionally provides a method for evaluating the severity of abdominal aortic aneurysm (AAA) or risk of AAA in a subject. In one embodiment, the method comprises (a) contacting a test sample from the subject with an assay device capable of measuring the amount of $H_4B$ present in the test sample; (b) measuring the amount of $H_4B$ present in the test sample; and (c) comparing the measured amount of $H_4B$ present in the test sample to a measured amount of $H_4B$ present in a standard. The extent of decrease in the amount of $H_4B$ present in the test sample compared to the standard is indicative of the severity or risk of AAA in the subject. In some embodiments, a statistically significant decrease in the amount of $H_4B$ present in the test sample compared to the standard is indicative of AAA or predisposition to AAA. In other embodiments, the decrease in $H_4B$ is at least about a 10% decrease compared to the standard, or at least a 20%, 30%, 40%, 50% or 60%, 70%, 80% or 90% decrease. Smaller decreases are generally indicative of a predisposition to, or a milder case of AAA, while larger decreases are more likely to indicate the presence of AAA, or a more severe case of AAA. Depending on the amount of $H_4B$ present in the test sample, the subject may be monitored or treated as described herein.

In a typical embodiment of the invention, the sample comprises serum or whole blood, but it can be any body fluid. In a typical example, 2 ml of whole blood is drawn from the subject, although less than about 0.5 ml can be sufficient. The sample can be collected in a variety of conditions, including with or without spin down at the time of collection. Samples can be processed using, for example, a variety of collection tubes including supplement free, EDTA-containing, Heparin containing, and other conditions known in the art. Likewise, samples can be collected and stored under a variety of conditions, including, for example, by snap-freezing in liquid nitrogen; freezing at −20° C. for a couple of weeks and then transferred to −70° C. or −80° C.; or freezing at −70° C. or −80° C. and storing samples from there.

Assay Devices and Kits

In a typical embodiment, the assay device comprises a high performance liquid chromatography (HPLC) column, or an immunoassay kit, such as an enzyme-linked immunosorbent assay (ELISA) kit, a chemiluminescence assay kit, or other conventional assay kit. In a typical embodiment, the HPLC is equipped with a fluorescent or electrochemical detector and a C-18 column.

For use in the methods described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise one or more reagents for use in detecting $H_4B$ that is, optionally, detectably labeled. The kit can also include one or more containers for a reporter-means, such as a biotin-binding protein, e.g., avidin or streptavidin, bound to a detectable label, e.g., an enzymatic, florescent, or radioisotope label for use in detecting $H_4B$.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific application, and can also indicate directions for use. Directions and or other information can also be included on an insert which is included with the kit.

Administration and Dosage

The compositions are administered in any suitable manner, often with pharmaceutically acceptable carriers, excipients, or in the form of a pharmaceutically acceptable salt. Suitable methods of administering treatment in the context of the present invention to a subject are available, and, although more than one route can be used to administer a particular composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to elicit an effective response and/or to alleviate, reduce, cure or at least partially arrest symptoms and/or complications from the disease. An amount adequate to accomplish this is defined as a "therapeutically effective dose." In general, for pharmaceutical compositions comprising folic acid, the amount present in a dose ranges from about 1 to about 100 mg per kg of body weight of the subject, and higher. Representative amounts include, but are not limited to, 1, 5, 15, 30, 100 or higher mg/kg body weight. Suitable amounts will vary with the size of the patient, but will typically range from about 1-20 mg/tablet or 0.1 mL to about 5 mL.

Routes and frequency of administration of the therapeutic compositions disclosed herein, as well as dosage, will vary from individual to individual, and may be readily established using standard techniques. In general, the pharmaceutical compositions may be administered orally, or by injection (e.g., intracutaneous, intratumoral, intramuscular, intravenous or subcutaneous), intranasally (e.g., by aspiration). Typically, at least 1 to 10 doses may be administered over a 52 week period. Preferably, 6 doses are administered, at intervals of 1 month, and additional supplements may be given periodically thereafter. Alternate protocols may be appropriate for individual patients. In one embodiment, 2 or more oral supplements are administered 10 days apart. When treating with folic acid, it is typically best taken daily.

In general, an appropriate dosage and treatment regimen provides the active agent(s) in an amount sufficient to provide therapeutic and/or prophylactic benefit. Such a response can be monitored by establishing an improved clinical outcome in treated patients as compared to non-treated patients.

Treatment includes prophylaxis and therapy. Prophylaxis or therapy can be accomplished by a single administration at a single time point or multiple time points to a single or multiple sites. Administration can also be nearly simultaneous to multiple sites. Patients or subjects include mammals, such as human, bovine, equine, canine, feline, porcine, and ovine animals. The subject is preferably a human.

EXAMPLES

The following examples are presented to illustrate the present invention and to assist one of ordinary skill in making and using the same. The examples are not intended in any way to otherwise limit the scope of the invention.

Example 1: Role of Uncoupled Endothelial Nitric Oxide Synthase in AAA Formation

This example demonstrates a causal role of eNOS uncoupling/tetrahydrobiopterin deficiency in AAA formation. Therefore, oral folic acid administration, endothelium-targeted dihydrofolate reductase gene therapy, and perhaps other countermeasures directed against eNOS uncoupling could be used as new therapeutics for AAA.

By producing nitric oxide ($NO^{\bullet}$) to rapidly inactivate superoxide ($O_2^{\bullet-}$) and other reactive oxygen species (ROS), endothelial NO synthase (eNOS) protects vascular cells from oxidative damage. Accumulating evidence has demonstrated that, when eNOS cofactor tetrahydrobiopterin ($H_4B$) is deficient, eNOS becomes dysfunctional to produce $O_2^{\bullet-}$ rather than $NO^{\bullet}$.[1-13] This uncoupling of eNOS could deteriorate endothelial dysfunction, making it extremely difficult to correct. One important pathological agonist capable of transforming eNOS into the uncoupled state is angiotensin II (Ang II).[1,2,5] As previously shown, Ang II uncouples eNOS via transient activation of NADPH oxidase and consequent hydrogen peroxide-dependent, endothelium-specific deficiency in $H_4B$ salvage enzyme dihydrofolate reductase (DHFR).[1,5]

Ang II plays an important role in the pathogenesis of vascular diseases, such as hypertension and atherosclerosis, acting via well-characterized mechanisms, such as vasoconstriction, activation of vascular NADPH oxidase, and ROS dependent inflammatory and hypertrophic signaling.[14-18] Uncoupling of eNOS, however, represents a novel mechanism whereby Ang II causes prolonged oxidative stress.[1,2,5] Nevertheless, it has remained unclear whether uncoupled eNOS is directly involved in the pathogenesis of vascular disease. Tetrahydrobiopterin ($H_4B$) deficiency subsequent to a mutation in GTP cyclohydrolase 1 (GTPCH1) induces hyperphenylalaninemia in mice.[19,20] At baseline, hyperphenylalaninemia (hph)-1 mice have reduced $NO^{\bullet}$ bioavailability but preserved vasorelaxation because of hydrogen peroxide-dependent compensation.[19] After crossing with C57BL6 mice for >10 generations, the hph-1 mice have been genotyped and characterized using electron spin resonance for detection of $O_2^{\bullet-}$ production. Although in the wild-type (WT) animals NG-nitro-L-arginine methyl ester (L-NAME) increased $O_2^{\bullet-}$ production because of the loss of $NO^{\bullet}$, L-NAME attenuated $O_2^{\bullet-}$ production in hph-1 mice, implicating uncoupling of eNOS. Therefore, hph-1 mice can serve as an excellent model system to study contribution to vascular pathogenesis of uncoupled eNOS/$H_4B$ deficiency.

To examine whether uncoupled eNOS exaggerates pathological effects of Ang II to amplify hypertension or augment vascular remodeling, WT and hph-1 mice were infused with Ang II for 14 days. Mean blood pressure (MBP) monitored by an intracarotid telemetry method was found increased in both groups up to day 6 to 7. Although MBP in WT mice continued to rise, it started to decline in hph-1 mice, which was associated with sudden death (13.9%; n=72). Immediate postmortem inspection revealed rupturing abdominal aortic aneurysm (AAA). Approximately 65% of the surviving hph-1 s developed AAA, resulting in a total morbidity rate of 79% (n=72). AAA was further characterized and it was revealed that progressive DHFR deficiency and uncoupling of eNOS in Ang II-infused hph-1 underlie extensive vascular remodeling, inflammation, and AAA formation. Intriguingly, restoration of DHFR expression by oral administration of folic acid (FA), or overexpression of DHFR, completely prevented AAA formation in Ang II-infused hph-1 mice. These treatments also blunted progressive uncoupling of eNOS, as well as vascular remodeling and inflammation characterized by matrix metalloproteinase (MMP) activation, elastin breakdown, collagen remodeling, and macrophage infiltration. Therefore these innovative findings represent first evidence that eNOS uncoupling/$H_4B$ deficiency plays a causal role in AAA formation and that oral FA administration, DHFR-targeted therapy, and perhaps other countermeasures directed against eNOS uncoupling could serve as novel and powerful therapeutic regimes for AAA, the severe and prevalent human disease for which no pharmacological treatment is currently available.

Methods

Animals, Ang II Infusion, and Blood Pressure Measurements

The hph-1 mice (originally in CBA background)[19] were backcrossed with C57BL6 mice for >10 generations and genotyped based on a protocol by Khoo et al.[21] Only homozygote hph-1 mice in C57BL6 background were used for experiments. WT and hph-1 male mice at 24 weeks of age were infused with Ang II (0.7 mg/kg per day) using subcutaneously implanted osmotic pumps (Durect Corp). During the 14-day infusion, blood pressure was monitored by telemetry method. Wireless blood pressure probes were implanted into the animals 10 days before the implantation of the osmotic pumps. The catheter of the blood pressure probe was inserted into the left carotid artery, whereas the body of the probe was inserted into the right flank.

Animals were given 1 week to recover from the surgery. After this period, blood pressure was measured for 3 days to obtain a baseline. The osmotic pumps were then implanted on day 10 after surgery. Measurements were made daily from 9:00 AM to 4:00 PM at a 250-Hz sampling rate. Average blood pressure was calculated daily as the average of the entire recording period. The use of animals and experimental procedures were approved by the institutional animal care and usage committee at the University of California Los Angeles. Electron spin resonance determination of aortic NO and superoxide production, high-performance liquid chromatography determination of aortic $H_4B$ content, and Western blot determination of endothelial DHFR expression were performed as published previously.[1,2,5]

Endothelial Cell Isolation from Mouse Aortas

On harvest, whole aorta was cut open longitudinally and then digested with collagenase (0.6 mg/mL) at 37° C. for 20 minutes before gentle removal of endothelial cells with a cotton applicator. The supernatant containing endothelial cells was centrifuged and lysed for Western blot analysis.

Oral Administration of FA and DHFR Overexpression

WT and hph-1 mice were started on continuous oral administration of FA (15 mg/kg per day) or tail vein transfection of DHFR expression vector (pcDNA3.1-DHFR)5 in lipid-based reagent from Altogen Biosystems every other day for 14 days, starting 2 days before Ang II infusion. The mice were monitored twice per day during the infusion period of 2 weeks, and aortas were harvested for assessment of AAA formation, endothelial DHFR expression, and eNOS uncoupling activity by day 14. Animals that died suddenly during the infusion period of 14 days were inspected for aneurysm immediately and aortas were freshly harvested for experiments.

Ultrasound Detection of Abdominal Aorta Size

Animals were anesthetized with isoflurane and placed on a temperature-controlled table, which also measures ECG for heart rate. Isoflurane levels were adjusted throughout the experiment to maintain heart rate between 400 and 500 bpm while keeping the animal sufficiently anesthetized. Hair was removed from the abdomen using a hair removal cream, and preheated ultrasound transmission gel was applied onto the abdomen area. An ultrasound probe (Velvo 770, Visualsonics) was placed on the gel to visualize aorta transversely. The aorta was identified using Doppler measurement for the presence of pulsatile flow. Consistent localization of image acquisition was insured by visualizing the aorta immediately superior to the branch of the left renal artery in all of the animals. Images were recorded and saved onto a PC computer for offline area analysis. Hematoxylin-eosin and Verhoeff-Van Gieson stainings were conducted following standard histological protocols.

Macrophage Stainings

Formalin-fixed and paraffin-embedded tissue were sectioned at 5 µm. Paraffin was removed by washing with xylene and then rehydrated with descending concentrations of ethanol. Antigen retrieval was performed by immersing the sections in an antigen retrieval buffer (10 µmol/L of citric acid, 0.01% Tween 20) at 98.5° C. for 20 minutes. Sections were washed in PBS plus 0.1% triton (PBS-T) and then blocked with 2% normal goat serum in PBS-T at room temperature for 3 hours. Sections were then incubated with primary antibody (Mac-3, BD Pharmingen, 2%, in PBS-T) overnight at 4° C. After washing with PBS-T for 1 hour, sections were incubated with secondary antibody (Alexa fluor 488, 2% in PBS-T) for 2 hours at room temperature in the dark. After washing with PBS-T for 1 hour, sections were dehydrated with ascending grades of ethanol and then xylene. Sections were mounted with Permount medium and pictures taken with a confocal microscope (Leica, SP1 inverted). MMP activity assays were performed as published previously.[22]

Statistical Analysis

Comparisons among different treatment groups were performed by ANOVA. When differences were indicated, the Dunnet post hoc test was used. Statistical significance was set for $P<0.05$. All of the grouped data shown in the figures were presented as mean±SEM.

Results

Ang II Infusion of hph-1 Mice Induces AAA Formation

Twenty-four-week-old male WT (n=72) and hph-1 mice (n=72) were infused with Ang II (0.7 mg/kg per day) for 14 days. Approximately 14% of Ang II-infused hph-1 mice died suddenly of ruptured AAA within 14 days (FIG. 1B). Among the survivors, 65% developed AAA, resulting in a total morbidity rate of 79% (FIG. 1A-1B). In contrast, none of the Ang II-infused WT mice or untreated hph-1 mice died or developed AAA (FIG. 1A). The MBP was monitored by an intracarotid telemetry method and was found modestly higher in hph-1 mice as compared with WT mice at baseline (i.e., day 0 Ang II infusion; FIG. 1C). During Ang II infusion, MBP was increased in both genotypes up to day 6 (WT: 101±3-140±2 mm Hg; hph-1: 112±3-140±2 mm Hg; FIG. 1C). Thereafter, MBP declined in hph-1 mice, whereas it continued to rise in WT mice (FIG. 1C).

Figures 2A, 2B, 2C:
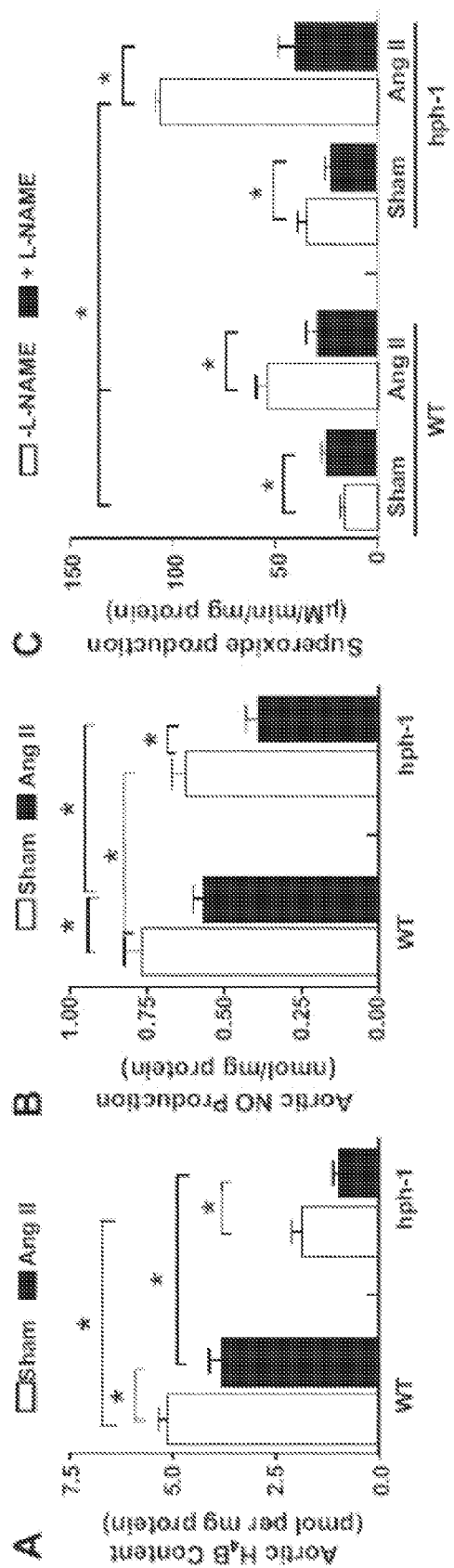
FIGS. 2A-C are bar graphs showing that Angiotensin II (Ang II) infusion augments deficiencies of tetrahydrobiopterin ($H_4B$) and $NO^{\bullet}$, and aggravates endothelial NO synthase (eNOS) uncoupling in hyperphenylalaninemia (hph)-1 mice. Wild-type and hph-1 mice were infused with Ang II (0.7 mg/kg per day) for 14 days, after which aortas were harvested for the following.

Ang II Infusion Augments Deficiency of $H_4B$ and NO$^\bullet$ and Aggravates eNOS Uncoupling, in hph-1 Mice Freshly isolated aortas from Ang II-infused WT and hph-1 mice were subjected to high-performance liquid chromatography determination of $H_4B$ content and electron spin resonance determination of NO$^\bullet$ and $O_2^{\bullet-}$ production.[1,2] As compared with WT mice, the hph-1 mice exhibited reduced aortic $H_4B$ bioavailability (FIG. 2A), which was further diminished by Ang II infusion (1.9±0.2-1.0±0.1 pmol/mg of protein; FIG. 2A). Ang II infusion also significantly reduced aortic $H_4B$ bioavailability in WT mice (5.1±0.2-3.8±0.4 pmol/mg of protein). Of note, aortic $NO^\bullet$ production mirrored these changes in Ang II-infused WT and hph-1 mice (FIG. 2B). Aortic $O_2^{\bullet-}$ production was determined in the presence or absence of L-NAME. Basal $O_2^{\bullet-}$ production was twice as high in hph-1 mice as compared with WT mice (FIG. 2C, compare sham hph-1 versus sham WT). Although L-NAME increased $O_2^{\bullet-}$ production as a result of inhibiting coupled eNOS in untreated WT mice (FIG. 2C), L-NAME decreased $O_2^{\bullet-}$ production in Ang II-infused WT mice, consistent with uncoupling of eNOS in response to Ang II, as reported previously[1,5] (FIG. 2C). In hph-1 mice, L-NAME decreased $O_2^{\bullet-}$ production in untreated mice, consistent with uncoupling of eNOS at baseline, in the absence of Ang II infusion (FIG. 2C). Importantly, Ang II infusion further uncoupled eNOS in hph-1 mice, as demonstrated by the substantially higher production of $O_2^{\bullet-}$ that was completely inhibited by L-NAME (FIG. 2C).

Figures 3A, 3B, 3C:
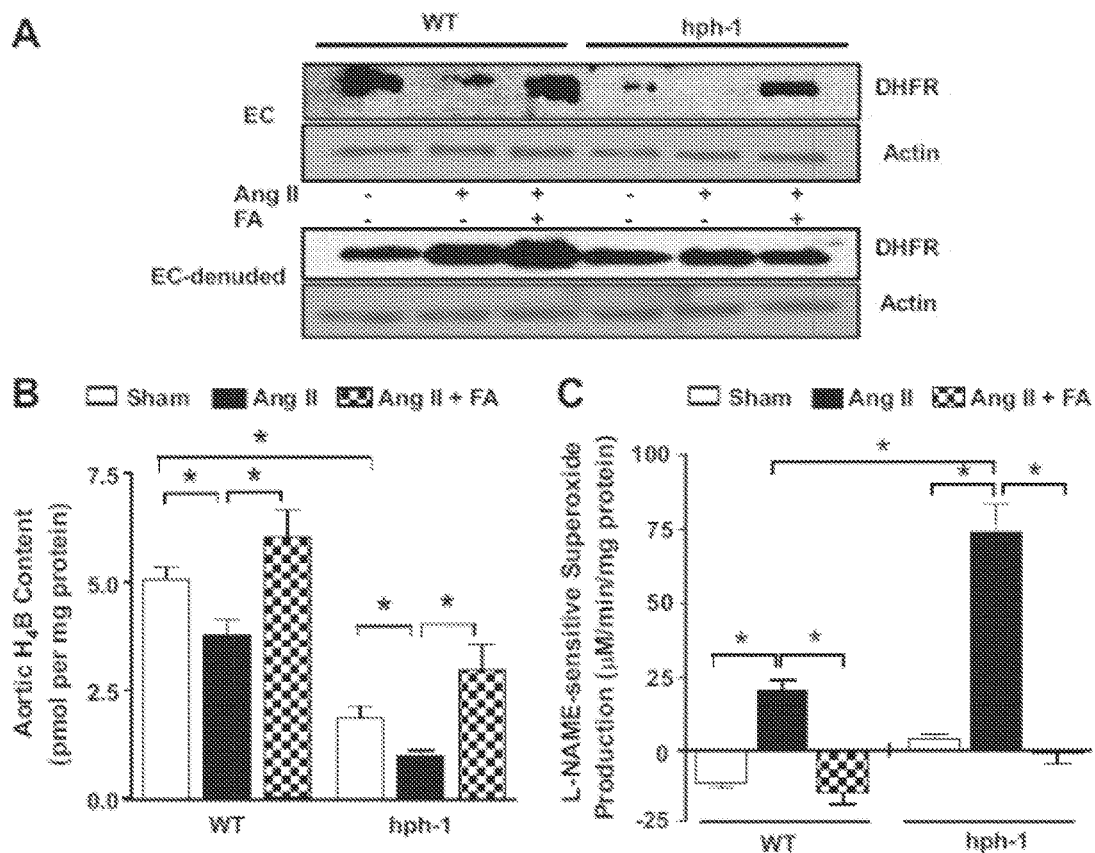
FIGS. 3A-C show that folic acid (FA) prevents endothelial NO synthase (eNOS) uncoupling in angiotensin II (Ang II)-infused hyperphenylalaninemia (hph)-1 mice via restoration of endothelial dihydrofolate reductase (DHFR) expression. Wild-type and hph-1 mice were started on oral administration of FA (15 mg/kg per day) 2 days before Ang II infusion (0.7 mg/kg per day) and treated throughout the study period of 14 days, after which aortas were harvested for the following.

FA Restores Endothelial DHFR Expression and $H_4B$ Bioavailability and Prevents eNOS Uncoupling in Ang II-Infused hph-1 Mice WT and hph-1 mice were started on oral FA (15 mg/kg per day) 2 days before Ang II infusion (0.7 mg/kg per day) and treated throughout the study period of 14 days. Both endothelial cells (digested off aortas, see Methods section) and endothelial cell-denuded aortas were analyzed for DHFR expression. As shown, hph-1 mice exhibited reduced endothelial DHFR expression, which was further reduced by Ang II infusion. FA treatment restored endothelial DHFR expression in hph-1 mice to near WT levels (FIG. 3A). The $H_4B$ deficiencies induced by Ang II in both WT and hph-1 mice were likewise prevented by FA treatment, resulting in $H_4B$ levels that were even higher than baseline in both groups (FIG. 3B). Moreover, FA prevented eNOS uncoupling in both Ang II-infused WT and hph-1 mice, as evidenced by complete attenuation of L-NAME-sensitive $O_2^{\bullet-}$ production (FIG. 3C).

Figures 4A, 4B, 4C, 4D, 4E, 4F:
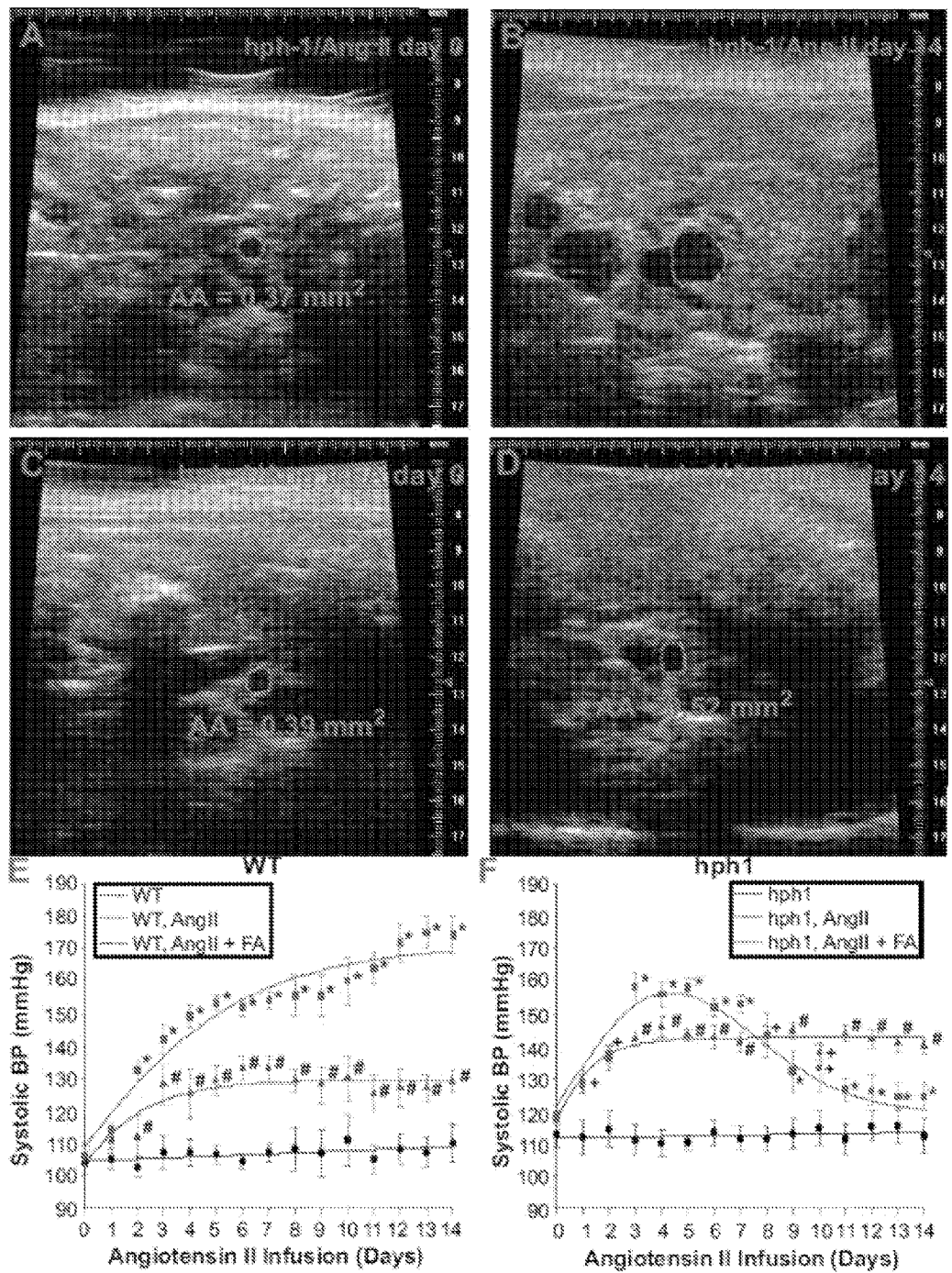
FIGS. 4A-F show that folic acid (FA) prevents abdominal aortic aneurysm (AAA) formation and normalizes blood pressure in angiotensin II (Ang II)-infused hyperphenylalaninemia (hph)-1 mice. Wild-type (WT) and hph-1 mice were started on oral administration of FA (15 mg/kg per day) 2 days before Ang II infusion (0.7 mg/kg per day) and treated throughout the study period of 14 days. At days 0 and 14, abdominal ultrasound (Velvo 770 high-resolution echo system, Visualsonics) was performed to assess abdominal aorta (AA) dimensions (FIGS. 4A-D) in Ang II-infused wild-type and hph-1 mice treated with or without FA. Aortic cross-sectional areas are depicted by blue circles, and calculated areas are listed below each image. Mean blood pressure (MBP) was assessed by telemetry during the course of the study (FIGS. 4E and 4F), as described in FIG. 1.

FA Treatment Prevents AAA Formation and Normalizes Blood Pressure in Ang II-Infused hph-1 Mice For this study, a total of 21 FA-treated Ang II-infused hph-1 mice was used, and none of these animals developed AAA. Statistical analysis using a 2×2 contingency table shows that this reduction in AAA development was significant (P<0.0001). On days 0 and 14, abdominal aorta dimensions were monitored using ultrasound (Velvo 770 high-resolution echo system equipped with a 45 MHz transducer, Visualsonics). Ang II infusion induced dramatic expansion of abdominal aorta in hph-1 mice (0.37-1.96 mm²), which was prevented by FA treatment (0.39-0.52 mm²; FIG. 4A through 4D). By contrast, in WT mice, Ang II induced a minimal increase in abdominal aorta size (0.53-0.66 mm²). In addition, FA was highly effective in attenuating Ang II-induced hypertension in WT mice (FIG. 4E), and it also prevented the decline in MBP in Ang II-infused hph-1 mice (FIG. 4F). These data suggest that, in WT mice infused with Ang II, uncoupling of eNOS leads to elevated MBP, most likely consequent to reduced $NO^\bullet$ bioavailability, whereas in hph-1 mice, which exhibit a more profound degree of eNOS uncoupling, the excessive production of ROS paradoxically lowers MBP, or that the reduction in MBP is mediated by ROS-independent mechanisms.

Figures 5A, 5B:
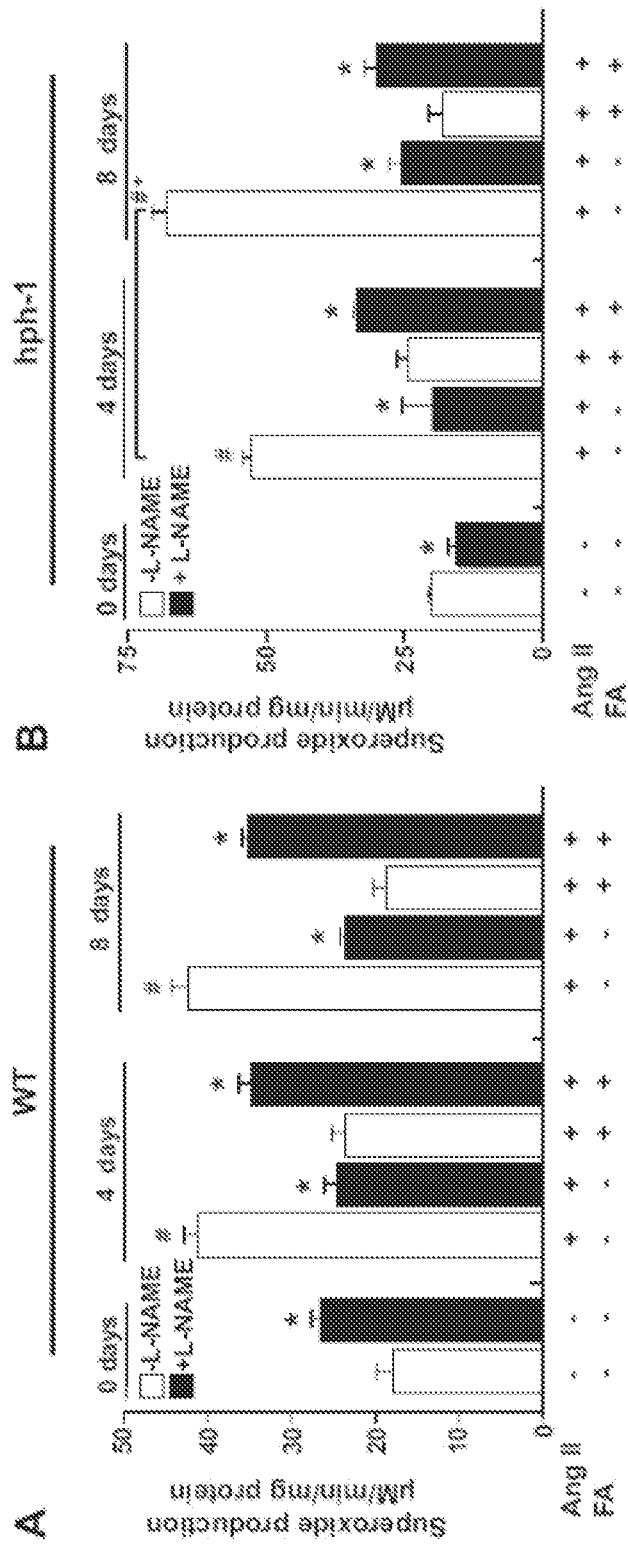
FIGS. 5A-B are bar graphs showing that folic acid (FA) prevents progressive uncoupling of endothelial NO synthase (eNOS) in angiotensin II (Ang II)-infused hyperphenylalaninemia (hph)-1 mice. Wild-type (WT) and hph-1 mice were started on oral administration of FA (15 mg/kg per day) 2 days before Ang II infusion (0.7 mg/kg per day) and treated throughout the study period of 14 days. Aortas were harvested on days 0, 4, or 8 for analysis of $O_2^{\bullet-}$ production in the presence or absence of NG-nitro-L-arginine methyl ester (L-NAME) in (FIG. 5A) WT and (FIG. 5B) hph-1 mice. *$P<0.05$ vs L-NAME, #$P<0.05$ vs WT sham, +$P<0.05$ vs 4 days.
Figures 6A, 6B, 6C:
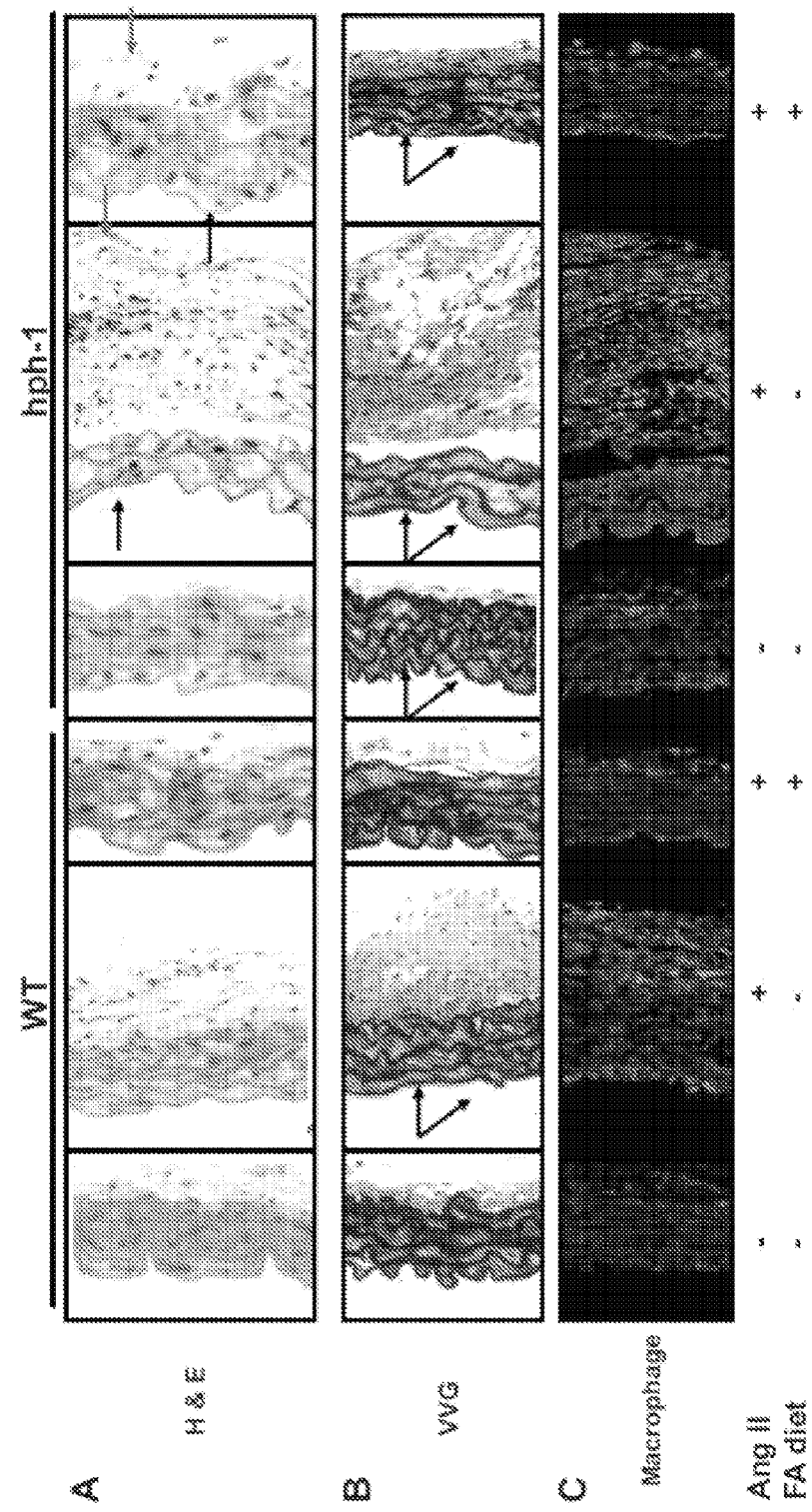
FIGS. 6A-C are photomicrographs showing that folic acid (FA) prevents vascular remodeling in angiotensin II (Ang II)-infused hyperphenylalaninemia (hph)-1 mice. Wild-type and hph-1 mice were treated with or without FA (15 mg/kg per day) beginning 2 days before Ang II (0.7 mg/kg per day) or vehicle infusion and treated throughout the study period of 14 days, after which aortas were harvested for (FIG. 6A) hematoxylin-eosin (H&E) staining (black arrows and red arrows indicating FA-induced changes in media and adventitia, respectively)
Figures 7A, 7B, 7C:
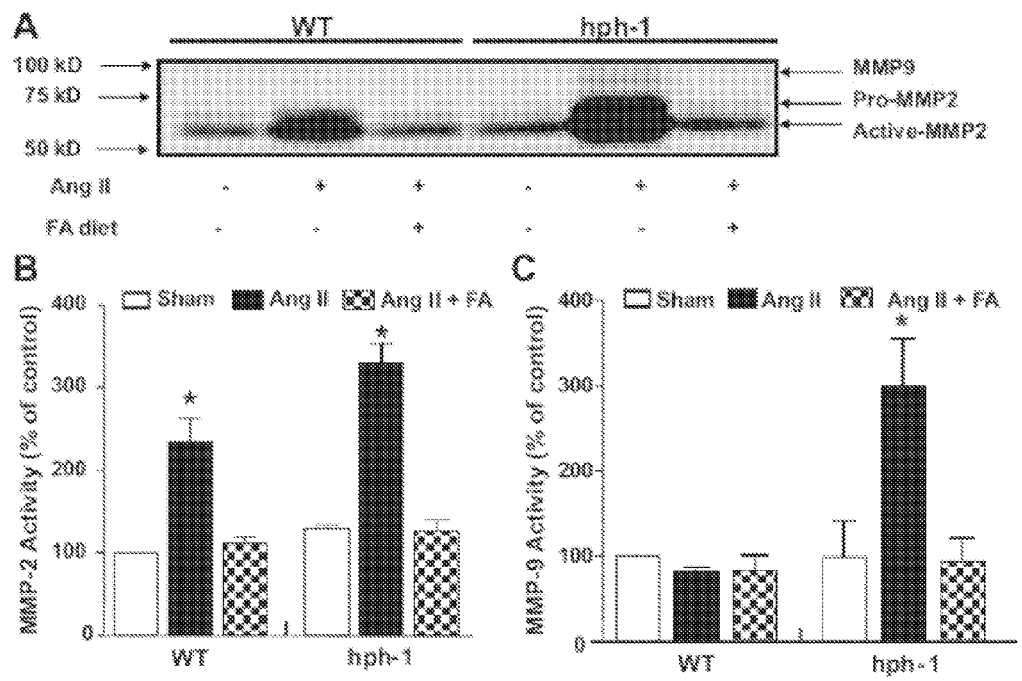
FIGS. 7A-C show that folic acid (FA) prevents angiotensin II (Ang II)-induced matrix metalloproteinase (MMP) 2 and MMP9 activation in hyperphenylalaninemia (hph)-1 mice. Wild-type and hph-1 mice were treated with or without FA (15 mg/kg per day) beginning 2 days before Ang II (0.7 mg/kg per day) or vehicle (sham) infusion. After the 14-day study period, aortas were harvested to assess MMP activity.

FA Prevents Progressive Uncoupling of eNOS and Vascular Remodeling in Ang II-Infused hph-1 Mice To examine the effects of FA on eNOS uncoupling at different time points during AAA development, $O_2^{\bullet-}$ production was followed on days 4 and 8 day after initiation of Ang II infusion. Aortas were harvested and subjected to electron spin resonance detection of $O_2^{\bullet-}$ in the presence or absence of L-NAME. In WT mice, eNOS uncoupling activity remained steady in response to Ang II for both time points examined. As is obvious in FIG. 5A, L-NAME-sensitive $O_2^{\bullet-}$ production that is reflective of eNOS uncoupling activity was similar on days 4 and 8. In contrast, Ang II induced progressive uncoupling of eNOS in hph-1 mice. As demonstrated in FIG. 5B, the L-NAME inhibitable fraction of $O_2^{\bullet-}$ production was augmented on day 8 compared with what was observed on day 4. Importantly, FA consistently suppressed eNOS uncoupling activity in hph-1 mice at both time points. In additional experiments, it was found that FA also prevented Ang II-induced vascular remodeling in hph-1 mice. As indicated by hematoxylin-eosin staining, FA abrogated medial degradation and adventitial inflammatory cell recruitment in Ang II-infused hph-1 mice (FIG. 6A). More specifically, FA attenuated medial elastin flattening and rarefaction of elastin fibers, as shown by Verhoeff-Van Gieson (VVG) staining (FIG. 6B). Infiltrating macrophages, one of the major sources of matrix degradation enzymes, including MMP9, were also dramatically upregulated with Ang II-infused mice, which was completely attenuated with FA treatment (FIG. 6C). Furthermore, FA attenuated Ang II-induced augmentation of MMP2 activation and MMP9 activation in hph-1 mice, whereas it also inhibited Ang II-induced MMP2 activation in WT mice (FIG. 7).

Figures 8A, 8B:
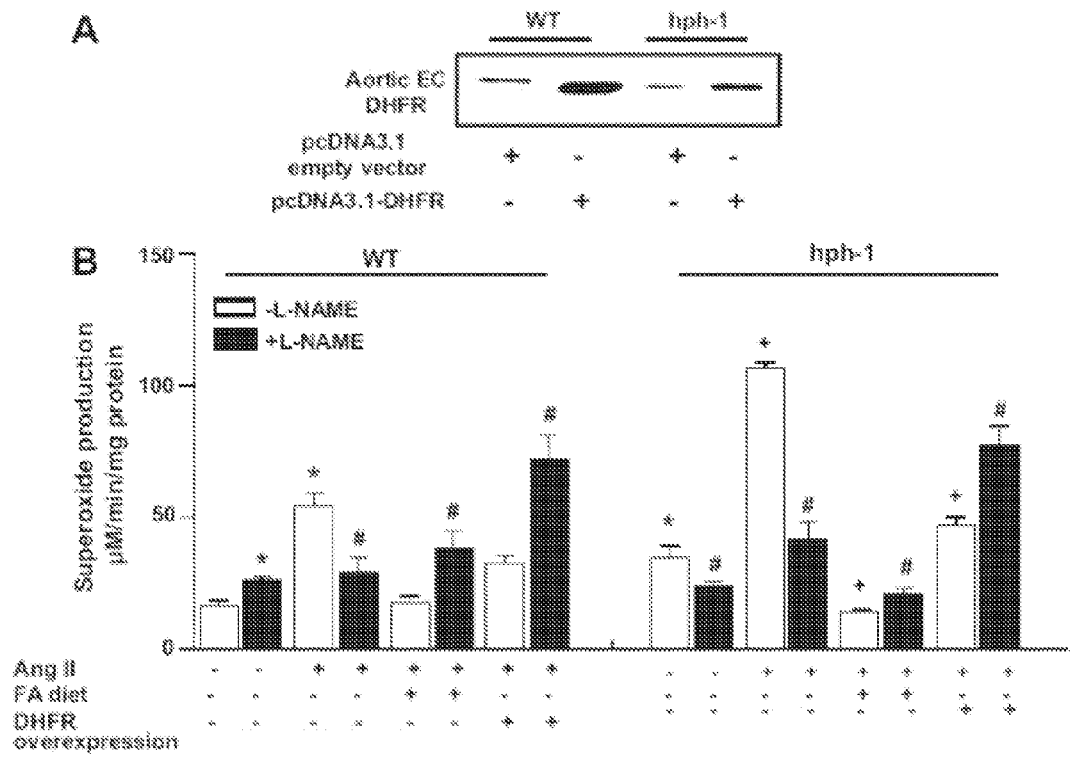
FIGS. 8A-B Dihydrofolate reductase (DHFR) overexpression recouples endothelial NO synthase (eNOS) in angiotensin II (Ang II)-infused hyperphenylalaninemia (hph)-1 mice. Wild-type (WT) and hph-1 mice were subjected to tail vein transfection of DHFR expression vector (pcDNA3.1-DHFR) in lipid-based reagent from Altogen Biosystems every other day for 14 days, starting 2 days before Ang II infusion. At the end of the 14 day infusion, aortas were harvested for (FIG. 8A) endothelial DHFR expression in aortic preparations by Western blotting and (FIG. 8B) aortic superoxide production in the presence or absence of NG-nitro-L-arginine methyl ester (L-NAME). *$P<0.05$ vs wild-type (WT) sham, #$P<0.05$ vs L-NAME, +$P<0.05$ vs hph-1 sham.

DHFR Gene Therapy Recouples eNOS and Prevents AAA Formation in Ang II-Infused hph-1 Mice As shown previously, DHFR gene therapy is effective in recoupling eNOS in Ang II-infused WT mice.[1] To test whether DHFR gene therapy is enough to overcome its deficiency in Ang II-infused hph-1 mice that is crucial for AAA formation, WT or hph-1 mice were transfected with DHFR before initiation of Ang II infusion and throughout the entire infusion period. Endothelial DHFR expression was markedly enhanced after successful in vivo transfection of a DHFR-containing expression vector (FIG. 8A),[5] and this was effective in completely attenuating augmented eNOS uncoupling in Ang II-infused hph-1 mice (L-NAME) instead of increased $O_2^{\bullet-}$ production as in WT controls (FIG. 8B). None of the Ang II-infused hph-1 mice in which DHFR was overexpressed developed AAA.

Discussion

The most significant finding of the present study is the first demonstration of a causal role of eNOS uncoupling/$H_4B$ deficiency and the therapeutic potential of eNOS recoupling, in AAA formation. In hph-1 mice where eNOS is uncoupled at baseline, Ang II infusion induces AAA formation in conjunction with further uncoupling of eNOS. Treatment with oral FA effectively prevented both eNOS uncoupling and AAA formation in hph-1 mice. Moreover, FA attenuated Ang II-induced vascular remodeling in both hph-1 and WT mice and modulated blood pressure responses to Ang II differentially in both groups of animals. These findings suggest that eNOS uncoupling predisposes to AAA formation and that strategies directed at eNOS recoupling could be of benefit in treating this vascular disorder.

Elevated parameters of oxidative stress have been detected both systemically and locally in human AAA.[23,24] Moreover, increased aortic oxidative stress has been reported in conjunction with AAA induced experimentally in animal models, and countermeasures against oxidative stress have proven effective in preventing AAA formation in Ang II-infused mice, although not in humans.[25-27] Despite a previously established role of vascular smooth muscle, whether other cellular or enzymatic sources of oxidative stress are involved in the pathogenesis of AAA, however, remains to be fully understood. This is the first report that uncoupled eNOS can contribute to oxidative stress leading to severe vascular remodeling and AAA formation in a murine model. The infrarenal pattern of the AAA is very similar to what is found in humans. In addition, the pathological features that observed in mice with uncoupled eNOS resemble those observed in human AAA, including adventitial inflammation, activation of MMPs, and matrix degradation (FIGS. 6 and 7). Moreover, the AAA was prone to rupture leading to sudden death, as demonstrated by a mortality rate of 14% in these Ang II-infused hph-1 mice (FIG. 1B). Of note, the uncoupling process makes eNOS a peroxynitrite generator, implicating that peroxynitrite, rather than other ROS, might serve as an important redox-signaling mediator for AAA formation. Deletion of eNOS in high-fat-fed apolipoprotein E null mice resulted in spontaneous AAA formation, although the incidence rate was much lower at 25%.[28,26] Notably, eNOS uncoupling has also been observed in apolipoprotein E-deficient mice at baseline.[7,30] Mice deficient in eNOS exhibit increased oxidative stress consequent to a loss in NO$^\bullet$ production. However, these mice do not develop eNOS uncoupling, because they lack functional eNOS protein. Taken together, these data suggest that an eNOS uncoupling-dependent NO$^\bullet$/ROS imbalance in the vasculature, rather than loss of NO$^\bullet$ production, per se, is more profoundly inductive of AAA formation. The data also suggest a novel role for endothelial cells in oxidant generation that is involved in promoting AAA formation.

Ang II infusion induced a rapid rise in blood pressure in the hph-1 mice, similar to what was observed in the WT mice. However, in hph-1 mice, blood pressure began to progressively fall after day 6 of Ang II infusion, reaching pretreatment values by day 11. In contrast, in WT mice, blood pressure continued to rise throughout the course of Ang II infusion. Treatment with FA, which has been demonstrated to recouple eNOS,[1,31,32] attenuated both the rise in blood pressure in WT mice and the fall in blood pressure in hph-1 mice resulted from Ang II infusion, suggesting the involvement of eNOS uncoupling in both responses. In the case of WT animals, the eNOS uncoupling induced by Ang II likely contributed to hypertension by reducing NO$^\bullet$ bioavailability. Reduced NO$^\bullet$ bioavailability likely also contributed to the increased blood pressure at baseline in hph-1 mice and to the initial pressor response to Ang II infusion (FIG. 1C). The subsequent fall in blood pressure in Ang II-infused hph-1 mice also appears to result from eNOS uncoupling, although the exact mechanism remains to be determined. It is possible that the growing aneurysm affects hemodynamics, hence, blood pressure. Modulation of blood pressure by oxidative stress is complex and dependent on the balance between destruction of NO$^\bullet$ and production of ROS that can have vasoconstrictor or vasodilator effects. For example, hydrogen peroxide has been shown to mediate compensatory vasodilatation in hypertensive animals.[6] Then scavenging of eNOS-derived hydrogen peroxide by recoupling of eNOS may increase vasocontractility and blood pressure. Considering that WT mice develop sustained hypertension but no AAA formation in response to Ang II infusion, whereas hph-1 mice develop AAA formation but only transient hypertension, the data are consistent with the previous notions that hypertension is not a decisive risk factor for AAA development, although it may facilitate the disease process.[28,29,33]

It was also important to note that eNOS was progressively uncoupled in Ang II-infused hph-1 mice but not in WT mice (FIG. 6), which is consistent with progressive DHFR deficiency in hph-1 mice that was fully corrected by FA treatment (FIG. 3A). These data indicate a critical role for endothelial DHFR deficiency in mediating eNOS uncoupling and AAA formation. DHFR is expressed in vascular cells other than endothelial cells; however, only endothelial DHFR abundance correlates with aortic H$_4$B and NO$^\bullet$ bioavailability (FIG. 3A).[1,5]

Previous studies have shown that MMPs, specifically MMP-2 and -9, are major players in the development of AAA.[34-36] In this study, an increase was observed in the activities of both of these enzymes in the Ang II-infused hph-1 animals (FIGS. 7B and 7C), which matches well with those earlier observations. Interestingly, MMP-2 activity was also increased in Ang II-infused WT animals, which did not develop AAA. This seems to suggest that MMP2 activation alone is not sufficient for AAA development. Of note, MMP-9 activity was found increased only in Ang II-infused hph-1 mice. Furthermore, macrophage staining (FIG. 6C) in these animals was dramatically more abundant than in the Ang II-infused WT animals. These findings are in agreement with previous observations that the source of MMP-9 in AAA is generally macrophages.[36] Taken together, the data suggest that Ang II infusion causes an increase in MMP-2 production in the aortas of both WT and hph-1 animals, mostly likely from vascular smooth muscle cells[34,36,37] and endothelial cells.[38,39] However, an increase in MMP-9 from stimulated vascular cells and infiltrating macrophages is necessary for AAA to occur.

These data innovatively suggest a causal role of eNOS uncoupling/H$_4$B deficiency in AAA formation and raise the possibility that oral FA administration, DHFR gene therapy, and perhaps other countermeasures directed against eNOS uncoupling could be of benefit in treating AAA.

References

A complete list of citations to references provided throughout Example 1 can be found in Gao et al., 2012, *Hypertension*. 59:158-166.

Example 2: Prevention of Abdominal Aortic Aneurysm Formation Via Dietary Folic Acid This example demonstrates that a FA supplemented diet can prevent the development of AAA in Ang II-infused apoE null mice via improvement of tissue H$_4$B levels and the recoupling of eNOS. The data presented in Example 1 show that FA is effective in abolishing the development of AAA in the Ang II-infused hph-1 animal model. In this Example, the treatment is tested in another AAA model to show that the protective effect of FA extends to other models. Further, this example tests whether FA exerts its protective effect via H$_4$B and the recoupling of eNOS.

Figure 11:
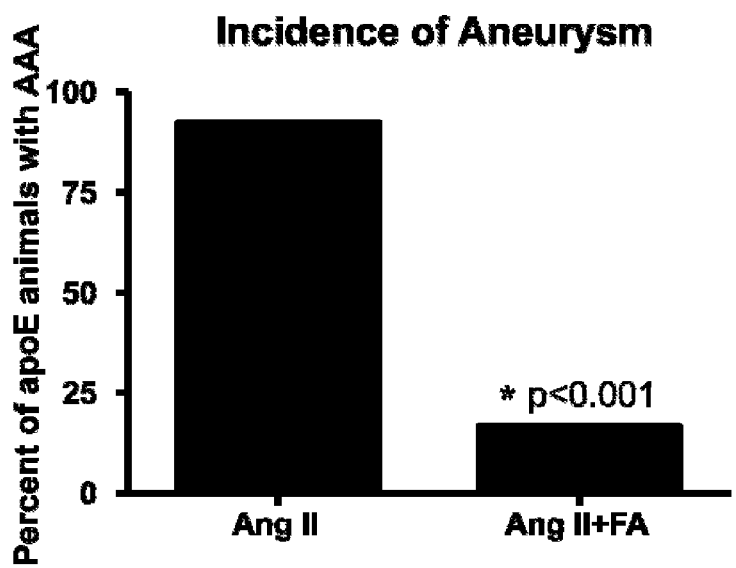
FIG. 11 is a bar graph showing that oral folic acid (FA) administration prevents abdominal aortic aneurysm (AAA) formation in Ang II-infused apoE null mice. Ang II infusion induced AAA in 92% of the mice studied, and this was substantially attenuated to 17% by oral administration of FA. In Ang II-infused hph-1 mice (79% incidence rate within 2 weeks vs. 4 weeks for apoE null mice), FA administration completely prevented AAA occurrence (0%).

Three to five month old apoE null mice were infused with Ang II (1000 ng/kg/min) for 4 weeks using implanted Alzet osmotic pumps. Animals were fed normal chow or customized FA chew (15 mg/kg/day) two days prior to Ang II infusion and throughout the study period of 4 weeks. Of note, 24 out of 26 Ang II infused apoE null mice (92.3%) on normal chow developed AAA (FIG. 11). With FA treatment, the incidence rate of AAA dropped to 4 out of 24 (16.7%). Aortic superoxide production determined by electron spin resonance showed a 2.67±0.15 fold increase with Ang II treatment in apoE null mice, which was attenuated to 1.75±0.01 fold by FA administration (n=6 each). L-NAME sensitive superoxide production, which reflects eNOS uncoupling activity, was also measured. Ang II treated apoE null mice have greatly increased eNOS dysfunction with 2.22±0.2 fold increase in L-NAME sensitive superoxide production, a marked exaggeration from the modest uncoupling of eNOS in apoE null mice at baseline of 1.17±0.06 fold. Treatment with FA restored eNOS function, resulting in −1.22±0.4 fold change in L-NAME sensitive superoxide, which indicates no superoxide production from eNOS. These data demonstrate that an oral treatment of FA is extremely effective in reducing the incidence of AAA in a second model of AAA of Ang II-infused apoE null mice. The data further suggest that this protective effect of FA is at least partly attributed to the restoration of eNOS function.

Experimental Design:

For this study, apoE null male animals were infused with Ang II for 4 weeks, which has been shown in literature to reliably produce AAA in 90-100% of the animals. One group of animals is fed food mixed with FA. AAA development is monitored using a noninvasive ultrasound technique during the infusion period. At the end of the four weeks, aortas from the animals were harvested and histology or biochemical assays were performed to assess for various markers of AAA and eNOS functional state.

An osmotic mini-pump (Alzet, model 2004) is implanted subcutaneously into the animals, containing either Ang II (1000 ng/kg/min) or vehicle. Animals were either given regular chow, or food pellets made in house mixed with FA (15 mg/kg/day). Aorta are carefully dissected and cleaned of connective tissue from the animals after euthanasia. Blood samples (~0.1 mL) are collected from each animal on a weekly basis and after euthanasia.

The development of AAA is monitored noninvasively via an ultrasound imaging system (Vevo 770, Visualsonics) during the Ang II-infusion period. The abdominal aortas were imaged transversely and identified via Doppler measurements for the presence of a major pulsatile flow. Consistent location along the aorta between animals is maintained by visualizing the aorta immediately superior to the branch of the left renal artery. Aorta size is later measured offline from images captured. Two measurements per week after Ang II infusion, as well as two measurements before the Ang II infusion (for control) are made. AAA is defined as an enlargement of the abdominal aorta by at least 50%, and later confirmed at the experimental end point. The AAA incidence for this model was also assessed by direct inspection of abdominal aorta at time of harvest, or post-mortem in those died of sudden rupture.

Histological and biochemical assays, such as MMP zymography, are used to assess the effectiveness of FA's protection against AAA. Histology of sections of the harvested aortas will be done to visualize the details of the abdominal aorta. Tissue is fixed in formaldehyde, embedded in paraffin, and sectioned at 5 μm. Standard H&E, Mason's trichrome, and VVG stains are performed.

An increase in MMP activity is one of the hallmarks of AAA development. Therefore, MMP activity can be measured using a zymography technique described in detail in other studies. Briefly, aortic lysates are loaded to gelatin infused SDS-PAGE gels. After electrophoresis, gelatin in the gel is digested by MMP in the loaded samples by incubating the gel in 37° C. overnight. Bands of lysis are then visualized with standard Coomassie blue staining.

$H_4B$ levels are measured using a HPLC system as previously described. Briefly, aorta samples are lysed with trichloroacetic acid and DTT, subjected to acidic or alkalytic oxidation, and $H_4B$ and its oxidized species are detected with a fluorescent detector after separation in the HPLC system (Shimadzu).

The functional state of eNOS is assessed in lysed aortic samples by measuring superoxide production in the presence or absence of L-NAME using electron spin resonance (ESR, from Bruker). Under normal conditions where eNOS is coupled, the addition of the eNOS inhibitor L-NAME will increase superoxide production, as eNOS is normally producing NO to scavenge superoxide. However, under eNOS uncoupled conditions where eNOS is producing superoxide, the addition of L-NAME will decrease superoxide production. This direction of change in superoxide production will allow for an accurate assessment of eNOS function in the aortas of the animals.

Figure 9A:
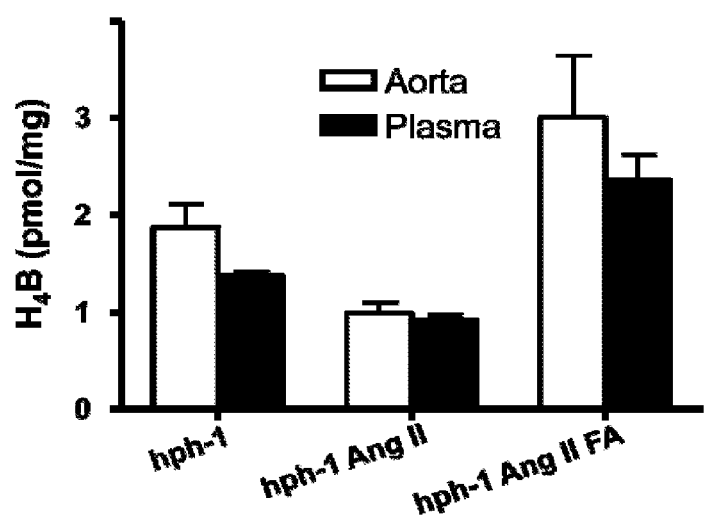
FIGS. 9A-B are bar graphs showing aortic and plasma levels of $H_4B$ in two different models of abdominal aortic aneurysm (AAA) in the presence or absence of folic acid (FA) therapy.
Figure 9B:
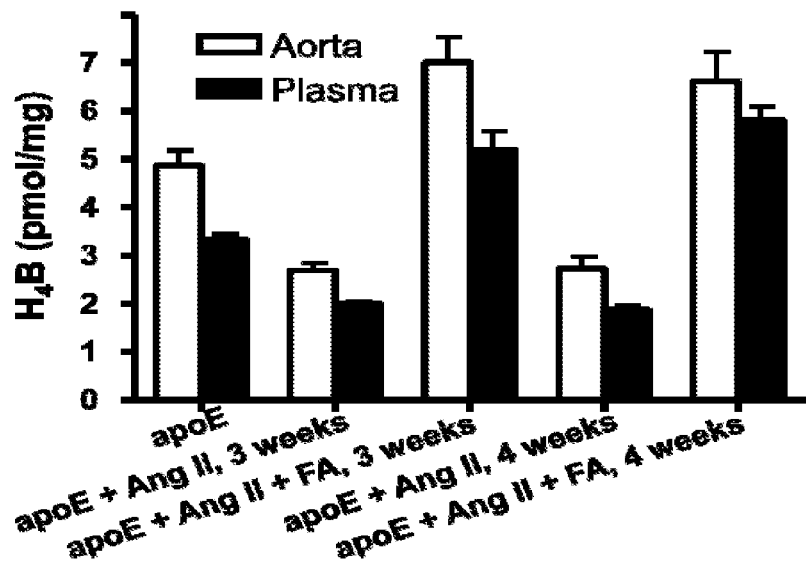

Example 3: Circulating $H_4B$ Levels as a Biomarker for AAA in hph-1 and apoE Null Mice This example demonstrates that $H_4B$ levels can be used as a biomarker for AAA. In this study, both hph-1 mice and another established AAA model of Ang II infused apoE null mice were studied. In apoE null mice, $H_4B$ measured using HPLC showed that in the aortas, $H_4B$ levels decreased with Ang II infusion (4.86±0.32 to 2.72±0.26 pmol/mg, n=6 each), and increased with oral administration of FA (6.60±0.62 pmol/mg, n=6). A similar trend was observed when $H_4B$ was measured from plasma (3.31±0.13, 1.87±0.11, 5.80±0.30 pmol/mg, vehicle, Ang II, FA, respectively, n=6 each). Identically in hph-1 mice, aortic levels of $H_4B$ came out to be at 1.87±0.25, 0.99±0.11, 3.00±0.64, and plasma levels being 1.37±0.05, 0.92±0.06, and 2.36±0.25 pmol/mg (for vehicle, Ang II & AngII/FA respectively, n=3 each). More complete and updated data are presented in FIGS. 9A-B and 11.

Figure 10A:
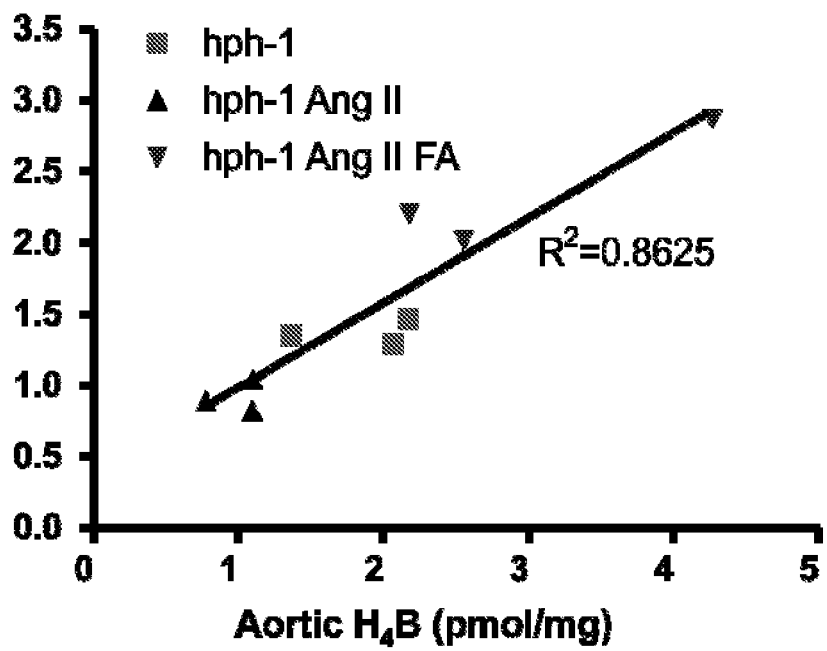
FIGS. 10A-B plot the correlation between aortic and plasma levels of $H_4B$ levels in two different models of abdominal aortic aneurysm (AAA) in the presence or absence of folic acid (FA) therapy.
Figure 10B:
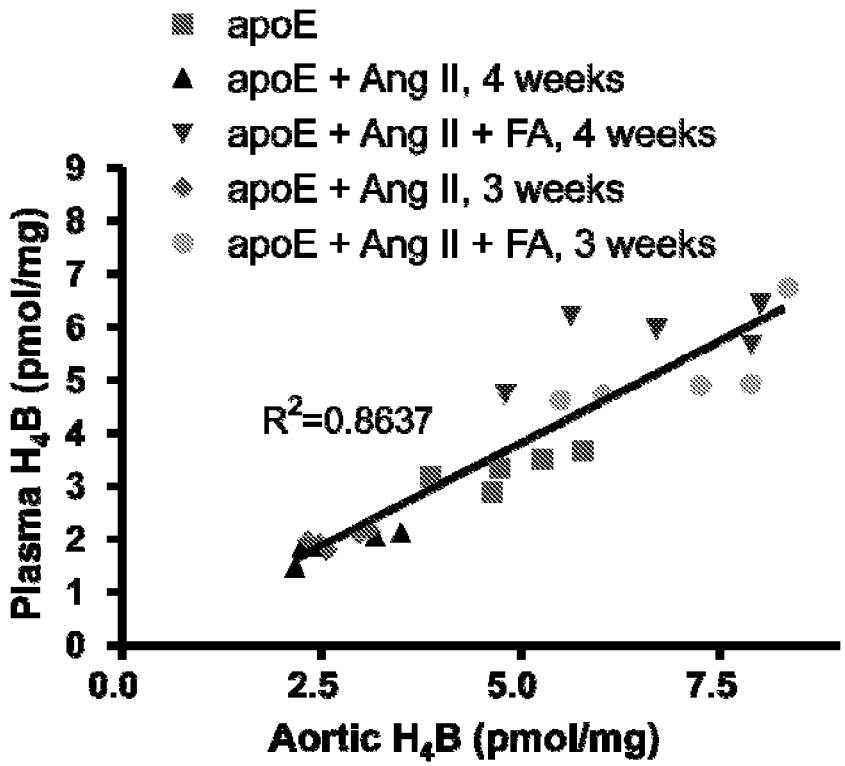

Further, linear correlation between plasma and aortic $H_4B$ levels shows a R2 of 0.86 for the apoE null mice, and also for the hph-1, suggesting a linear relationship between the two measurements. This linear relationship between the two measurements is extremely important, as this will allow for a less invasive method of measuring local vascular $H_4B$ bioavailability, which is believed to be essential for predicting AAA development. More complete and updated data are presented in FIGS. 10A-B.

These data indicate that a decreased $H_4B$ bioavailability is associated with AAA formation while a restored $H_4B$ bioavailability is associated with prevention of AAA development. Furthermore, changes in aortic $H_4B$ values are reflected in the plasma. Taken together, these data suggest that circulating $H_4B$ levels can serve as a biomarker for AAA development, as well as a predictor of treatment efficacies.

Experimental Design:

Blood samples are collected from Ang II-infused apoE null and hph-1 animals. Approximately 0.1 mL of blood is collected from each animal from the tail vein on a weekly basis. HPLC is used to determine the concentration of $H_4B$ in the blood samples as outlined above.

Also investigated was whether FA supplementation as used above leads to improved $H_4B$ availability both in the circulation and in the vascular tissues. Ang II-infused apoE null or hph-1 mice are treated with diets supplemented with FA, and circulating and aortic $H_4B$ contents are determined using HPLC at different time points of 1, 2, 3 and 4 wks. These data are correlated with development of AAA to examine how an actual improvement of $H_4B$ as a biomarker is linked to prevention of AAA. It is established that it takes 3-4 weeks for AAA to develop in Ang II-infused apoE null mice, and at these time points, circulating and tissues $H_4B$ levels were indeed decreased, but restored by FA treatment (FIGS. 9-10).

Figure 13A:
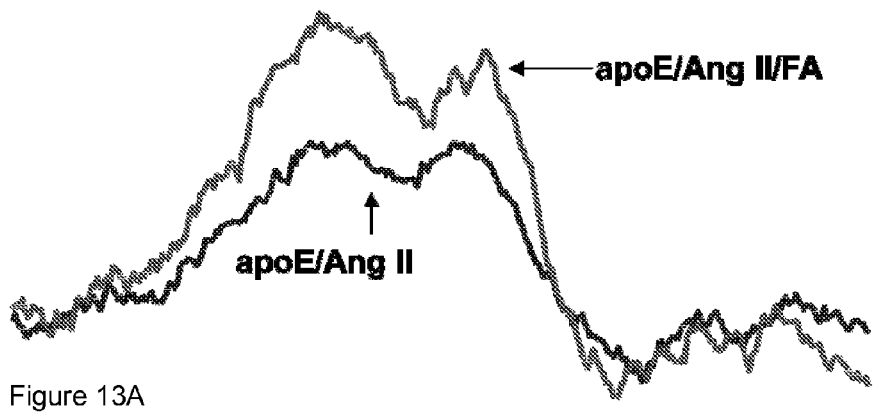
FIGS. 13A-B illustrate restoration of aortic nitric oxide (NO) bioavailability in Ang II-infused apoE null mice via oral folic acid (FA) administration. Aortic bioavailable nitric oxide (NO) radical was measured quantitatively and sensitively by electron spin resonance (ESR). Consistent with findings that FA completely recoupled eNOS in Ang II-infused apoE null mice, aortic nitric oxide (NO) bioavailability was also markedly improved by FA treatment.
Figure 13B:
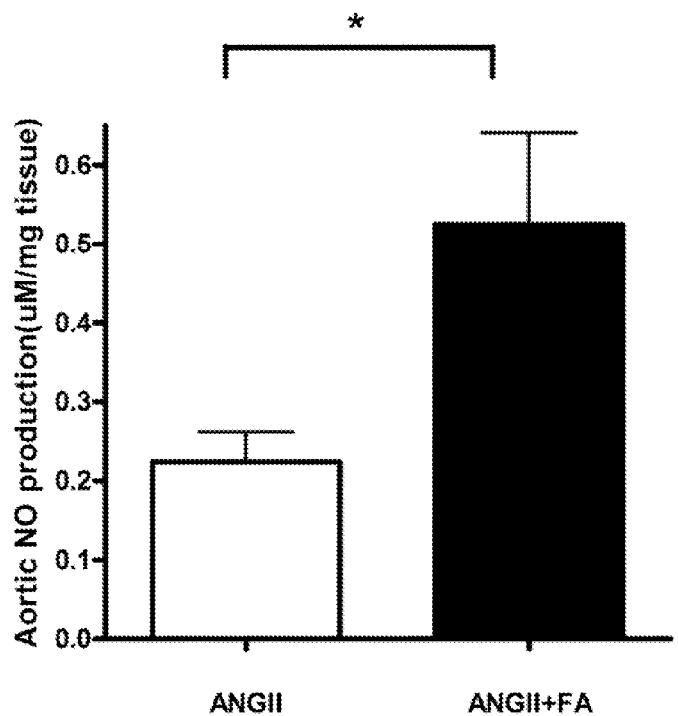

Example 4: Oral Folic Acid Administration Restores eNOS Function and Aortic NO Bioavailability in Ang II-Infused apoE Null Mice This example demonstrates that FA is highly effective in restoring eNOS function. Mice were infused with Ang II for 4 weeks (n=6) while a parallel group was orally treated with folic acid at 15 mg/kg/day 2 days prior to Ang II infusion and throughout the study period (n=6). A group of untreated apoE null mice (n=6) was also included. At baseline eNOS inhibitor L-NAME minimally reduced superoxide production, implicating a minor uncoupling/dysfunction of eNOS. Ang II infusion markedly increased L-NAME-sensitive superoxide production, which was completely abolished by oral administration of FA. Take together these data indicate that FA is highly effective in restoring eNOS function by restoring aortic and circulating $H_4B$ levels as shown in FIGS. 9 and 10, and by these mechanisms FA prevents AAA formation in Ang II-infused apoE null mice, a well established classical model of AAA (FIG. 11). FIG. 13 consistently demonstrates that nitric oxide (NO) bioavailability was also markedly improved by FA treatment as a result of restoration of eNOS function.

TABLE

Incidence of Aneurysm in apoE null Mice

| | AAA | No AAA | Total Number | Incidence |
|---|---|---|---|---|
| apoE + Ang II | 24 | 2 | 26 | 92.3% |
| apoE + Ang II + FA | 4 | 20 | 24 | 16.7% |

Figure 12:
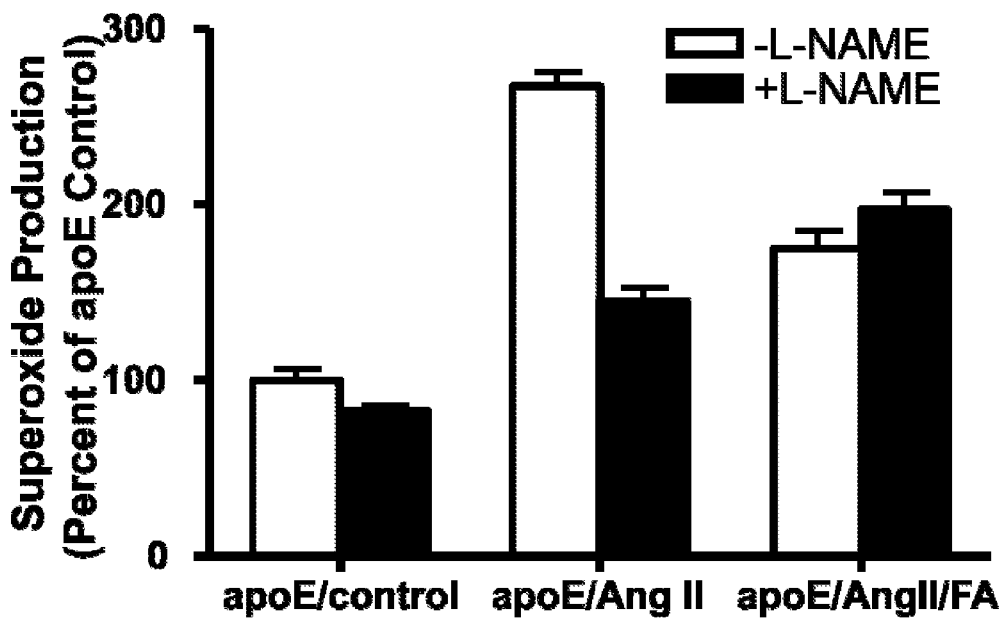
FIG. 12 is a bar graph showing that oral folic acid (FA) administration restores eNOS function in Ang II-infused apoE null mice. At baseline eNOS inhibitor L-NAME minimally reduced superoxide production, implicating a minor uncoupling/dysfunction of eNOS. Ang II infusion markedly increased L-NAME-sensitive superoxide production, which was completely abolished by oral administration of FA. These data indicate that FA is highly effective in restoring eNOS function/recoupling eNOS in Ang II-infused apoE null mice, which is similar to what is observed in Ang II-infused hph-1 mice.

Aortic bioavailable nitric oxide (NO) radical was measured quantitatively and sensitively by electron spin resonance (ESR). Consistent with findings that FA completely recoupled eNOS in Ang II-infused apoE null mice (FIG. 12), aortic nitric oxide (NO) bioavailability was also markedly improved by FA treatment. Top panel (FIG. 12A) shows representative ESR spectra of NO. Lower panel (FIG. 12B) shows grouped data of aortic NO levels (n=6). These data further support that an elevation in circulating/plasma levels of $H_4B$ is indeed correlated not only with aortic $H_4B$ levels (FIGS. 9 and 10), but also reduced AAA incidence (FIG. 11), as well as improved eNOS function and NO bioavailability (FIGS. 12 and 13).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for treating abdominal aortic aneurysm (AAA) in a subject, the method comprising:
    (a) contacting a test sample consisting of serum, plasma or whole blood from a subject with an assay device capable of measuring the amount of tetrahydrobiopterin ($H_4B$) present in the test sample, wherein the test sample is serum, plasma or whole blood;
    (b) measuring the amount of $H_4B$ present in the test sample, wherein the test sample has a decreased amount of $H_4B$ relative to a standard amount of $H_4B$; and
    (c) treating the subject for AAA with oral administration of folic acid.

2. The method of claim 1, wherein the assay device comprises a high performance liquid chromatography (HPLC) column.

3. The method of claim 1, wherein the assay device comprises an immunoassay kit.

4. The method of claim 1, wherein the decreased amount is a 20% decrease in the amount of $H_4B$ present in the test sample compared to the standard.

5. The method of claim 1, wherein the decreased amount is a 50% decrease in the amount of $H_4B$ present in the test sample compared to the standard.

6. The method of claim 1, wherein the sample is plasma.

7. The method of claim 1, further comprising:
    (c) contacting a second test sample from the subject obtained at a second time point with an assay device capable of measuring the amount of tetrahydrobiopterin ($H_4B$) present in the test sample;
    (d) measuring the amount of tetrahydrobiopterin ($H_4B$) present in the second test sample;
    wherein treatment with folic acid therapy is administered to the subject prior to the second time point.

8. The method of claim 7, wherein a 20% increase is measured in the amount of $H_4B$ present in the second test sample compared to the measured amount of step (b).

9. The method of claim 7, further comprising prescribing a modified treatment for AAA to the subject whose $H_4B$ is decreased in the second test sample compared to the measured amount of step (b).

10. The method of claim 9, wherein the $H_4B$ in the second test sample is decreased 50% compared to the standard.

11. A method for treating abdominal aortic aneurysm (AAA) in a subject, the method comprising:
    (a) measuring, in a test sample of serum, plasma or whole blood from the subject, the amount of tetrahydrobiopterin ($H_4B$) present in the test sample; wherein a 20% decrease is detected in the measured amount of $H_4B$ present in the test sample relative to a standard amount of $H_4B$; and
    (b) treating the subject with oral administration of folic acid.

12. The method of claim 1, wherein the decreased amount is a 30% decrease in the amount of $H_4B$ present in the test sample compared to the standard.

13. The method of claim 1, wherein the decreased amount is a 40% decrease in the amount of $H_4B$ present in the test sample compared to the standard.

14. The method of claim 11, wherein the decrease is a 30% decrease in the amount of $H_4B$ present in the test sample compared to the standard.

15. The method of claim 11, wherein the decrease is a 40% decrease in the amount of $H_4B$ present in the test sample compared to the standard.

16. The method of claim 11, wherein the decrease is a 50% decrease in the amount of $H_4B$ present in the test sample compared to the standard.

17. The method of claim 7, wherein a 30% increase is measured in the amount of $H_4B$ present in the second test sample compared to the measured amount of step (b).

18. The method of claim 7, wherein a 40% increase is measured in the amount of $H_4B$ present in the second test sample compared to the measured amount of step (b).

\* \* \* \* \*